(12) United States Patent
Lurie

(10) Patent No.: US 7,766,011 B2
(45) Date of Patent: Aug. 3, 2010

(54) POSITIVE PRESSURE SYSTEMS AND METHODS FOR INCREASING BLOOD PRESSURE AND CIRCULATION

(75) Inventor: Keith G. Lurie, Minneapolis, MN (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 1542 days.

(21) Appl. No.: 11/034,996

(22) Filed: Jan. 12, 2005

(65) Prior Publication Data

US 2005/0165334 A1 Jul. 28, 2005

Related U.S. Application Data

(63) Continuation of application No. 10/796,875, filed on Mar. 8, 2004, and a continuation-in-part of application No. 10/660,462, filed on Sep. 11, 2003, now Pat. No. 7,082,945, which is a continuation-in-part of application No. 10/460,558, filed on Jun. 11, 2003, now Pat. No. 7,185,649, which is a continuation-in-part of application No. 10/426,161, filed on Apr. 28, 2003, now Pat. No. 7,195,012.

(51) Int. Cl.
| | |
|---|---|
| A61M 16/00 | (2006.01) |
| A62B 9/02 | (2006.01) |
| A62B 18/02 | (2006.01) |
| A62B 18/08 | (2006.01) |
| A62B 18/10 | (2006.01) |
| A61H 31/02 | (2006.01) |
| A61H 31/00 | (2006.01) |

(52) U.S. Cl. .................. 128/203.11; 128/202.28; 128/202.29; 128/205.24; 128/205.25; 128/206.12; 128/206.15; 128/206.18; 128/206.21; 128/206.28; 128/207.12; 128/207.13; 128/207.16; 128/908; 601/41; 601/44

(58) Field of Classification Search ............ 128/202.28, 128/202.29, 203.11, 205.24, 205.25, 206.12, 128/206.15, 206.18, 206.21, 206.28, 207.12, 128/207.13, 207.16, 908; 601/41, 44
See application file for complete search history.

(56) References Cited

U.S. PATENT DOCUMENTS 2,774,346 A 12/1956 Halliburton (Continued)

FOREIGN PATENT DOCUMENTS

CA 668771 8/1963

(Continued)

OTHER PUBLICATIONS

Christenson, J.M., "Abdominal Compressions During CPR: Hemodynamic Effects of Altering Timing and Force", The Journal of Emergency Medicine, vol. 10, pp. 257-266, 1992.

(Continued)

*Primary Examiner*—Patricia M Bianco
*Assistant Examiner*—Nihir Patel
(74) *Attorney, Agent, or Firm*—Townsend and Townsend and Crew LLP

(57) ABSTRACT

In one embodiment, the invention provides a medical method for treating a person and comprises repeatedly compressing the person's chest. While repeatedly compressing the person's chest, the method further includes repeatedly delivering a positive pressure breath to the person and extracting respiratory gases from the person's airway using a vacuum following the positive pressure breath to create an intrathoracic vacuum to lower pressures in the thorax and to enhance blood flow back to the heart.

38 Claims, 13 Drawing Sheets

U.S. PATENT DOCUMENTS

| | | | |
|---|---|---|---|
| 3,077,884 A | 2/1963 | Batrow et al. | |
| 3,191,596 A | 6/1965 | Bird et al. | |
| 3,307,541 A | 3/1967 | Hewson | |
| 3,459,216 A | 8/1969 | Bloom et al. | |
| 3,515,163 A | 6/1970 | Freeman | |
| 3,662,751 A | 5/1972 | Barkalow et al. | |
| 3,669,108 A | 6/1972 | Sundblom et al. | |
| 3,794,043 A | 2/1974 | McGinnis | |
| 3,815,606 A | 6/1974 | Mazal | |
| 3,834,383 A | 9/1974 | Weigl et al. | |
| 3,933,171 A | 1/1976 | Hay | |
| 3,973,564 A | 8/1976 | Carden | |
| 4,041,943 A | 8/1977 | Miller | |
| 4,077,404 A | 3/1978 | Elam | |
| 4,166,458 A | 9/1979 | Harrigan | |
| 4,226,233 A | 10/1980 | Kritzer | |
| 4,259,951 A | 4/1981 | Chernack et al. | |
| 4,298,023 A | 11/1981 | McGinnis | |
| 4,316,458 A | 2/1982 | Hammerton-Fraser | |
| 4,320,754 A | 3/1982 | Watson et al. | |
| 4,349,015 A * | 9/1982 | Alferness | 601/41 |
| 4,397,306 A * | 8/1983 | Weisfeldt et al. | 601/41 |
| 4,446,864 A | 5/1984 | Watson et al. | |
| 4,449,526 A | 5/1984 | Elam | |
| 4,481,938 A | 11/1984 | Lindley | |
| 4,533,137 A | 8/1985 | Sonne | |
| 4,601,465 A | 7/1986 | Roy | |
| 4,809,683 A | 3/1989 | Hanson | |
| 4,827,935 A | 5/1989 | Geddes et al. | |
| 4,881,527 A | 11/1989 | Lerman | |
| 4,898,166 A | 2/1990 | Rose et al. | |
| 4,928,674 A | 5/1990 | Halperin et al. | |
| 4,971,042 A | 11/1990 | Lerman | |
| 5,014,698 A | 5/1991 | Cohen | |
| 5,016,627 A | 5/1991 | Dahrendorf | |
| 5,050,593 A | 9/1991 | Poon | |
| 5,056,505 A | 10/1991 | Warwick et al. | |
| 5,109,840 A | 5/1992 | Daleidon | |
| 5,163,424 A | 11/1992 | Kohnke | |
| 5,184,620 A | 2/1993 | Cudahy et al. | |
| 5,193,544 A | 3/1993 | Jaffe | |
| 5,217,006 A | 6/1993 | McCulloch | |
| 5,235,970 A | 8/1993 | Augustine | |
| 5,263,476 A | 11/1993 | Henson | |
| 5,295,481 A | 3/1994 | Geeham | |
| 5,301,667 A | 4/1994 | McGrail et al. | |
| 5,305,743 A | 4/1994 | Brain | |
| 5,316,907 A | 5/1994 | Lurie | |
| 5,355,879 A | 10/1994 | Brain | |
| 5,359,998 A | 11/1994 | Lloyd | |
| 5,377,671 A * | 1/1995 | Biondi et al. | 128/204.23 |
| 5,392,774 A | 2/1995 | Sato | |
| 5,398,714 A | 3/1995 | Price | |
| 5,423,772 A | 6/1995 | Lurie | |
| 5,454,779 A | 10/1995 | Lurie et al. | |
| 5,474,533 A | 12/1995 | Ward et al. | |
| 5,492,115 A | 2/1996 | Abramov et al. | |
| 5,492,116 A | 2/1996 | Scarberry et al. | |
| 5,496,257 A | 3/1996 | Kelly | |
| 5,517,986 A | 5/1996 | Starr et al. | |
| 5,549,581 A | 8/1996 | Lurie | |
| 5,551,420 A | 9/1996 | Lurie et al. | |
| 5,588,422 A | 12/1996 | Lurie | |
| 5,618,665 A | 4/1997 | Lurie | |
| 5,628,305 A | 5/1997 | Melker | |
| 5,632,298 A | 5/1997 | Artinian | |
| 5,643,231 A | 7/1997 | Lurie | |
| 5,645,522 A | 7/1997 | Lurie et al. | |
| 5,678,535 A | 10/1997 | DiMarco | |
| 5,685,298 A | 11/1997 | Idris | |
| 5,692,498 A | 12/1997 | Lurie et al. | |
| 5,704,346 A | 1/1998 | Inoue | |
| 5,722,963 A | 3/1998 | Lurie | |
| 5,730,122 A | 3/1998 | Lurie | |
| 5,735,876 A | 4/1998 | Kroll et al. | |
| 5,738,637 A | 4/1998 | Kelly et al. | |
| 5,782,883 A | 7/1998 | Kroll et al. | |
| 5,814,086 A | 9/1998 | Hirschberg et al. | |
| 5,823,185 A * | 10/1998 | Chang | 128/204.18 |
| 5,827,893 A | 10/1998 | Lurie | |
| 5,896,857 A | 4/1999 | Hely et al. | |
| 5,919,210 A | 7/1999 | Lurie | |
| 5,984,909 A | 11/1999 | Lurie | |
| 5,988,166 A | 11/1999 | Hayek | |
| 6,001,085 A | 12/1999 | Lurie | |
| 6,029,667 A | 2/2000 | Lurie | |
| 6,062,219 A | 5/2000 | Lurie et al. | |
| 6,078,834 A | 6/2000 | Lurie | |
| 6,155,257 A | 12/2000 | Lurie et al. | |
| 6,224,562 B1 | 5/2001 | Lurie et al. | |
| 6,234,985 B1 | 5/2001 | Lurie et al. | |
| 6,277,107 B1 | 8/2001 | Lurie | |
| 6,312,399 B1 | 11/2001 | Lurie et al. | |
| 6,425,393 B1 | 7/2002 | Lurie et al. | |
| 6,459,933 B1 | 10/2002 | Lurie et al. | |
| 6,463,327 B1 | 10/2002 | Lurie et al. | |
| 6,486,206 B1 | 11/2002 | Lurie | |
| 6,526,973 B1 | 3/2003 | Lurie et al. | |
| 6,578,574 B1 | 6/2003 | Kohnke | |
| 6,587,726 B2 | 7/2003 | Lurie et al. | |
| 6,604,523 B2 | 8/2003 | Lurie et al. | |
| 6,656,166 B2 | 12/2003 | Lurie | |
| 6,776,156 B2 | 8/2004 | Lurie et al. | |
| 6,792,947 B1 | 9/2004 | Bowden | |
| 6,863,656 B2 | 3/2005 | Lurie | |
| 6,935,336 B2 | 8/2005 | Lurie et al. | |
| 6,938,618 B2 | 9/2005 | Lurie et al. | |
| 6,986,349 B2 | 1/2006 | Lurie | |
| 7,044,128 B2 | 5/2006 | Lurie | |
| 7,082,945 B2 | 8/2006 | Lurie | |
| 7,174,891 B2 | 2/2007 | Lurie et al. | |
| 7,185,649 B2 | 3/2007 | Lurie | |
| 7,195,012 B2 | 3/2007 | Lurie | |
| 7,195,013 B2 | 3/2007 | Lurie | |
| 7,204,251 B2 | 4/2007 | Lurie | |
| 7,210,480 B2 | 5/2007 | Lurie et al. | |
| 7,275,542 B2 | 10/2007 | Lurie et al. | |
| 7,302,571 B2 | 11/2007 | Lurie et al. | |
| 7,311,668 B2 | 12/2007 | Lurie et al. | |
| 2001/0029399 A1 | 10/2001 | Orr et al. | |
| 2002/0069878 A1 | 6/2002 | Lurie et al. | |
| 2002/0170562 A1 | 11/2002 | Lurie et al. | |
| 2003/0000526 A1 | 1/2003 | Gobel | |
| 2003/0037784 A1 | 2/2003 | Lurie | |
| 2003/0062040 A1 | 4/2003 | Lurie | |
| 2003/0062041 A1 | 4/2003 | Lurie et al. | |
| 2003/0192547 A1 | 10/2003 | Lurie et al. | |
| 2004/0200473 A1 | 10/2004 | Lurie | |
| 2004/0200474 A1 | 10/2004 | Lurie | |
| 2004/0211415 A1 | 10/2004 | Lurie et al. | |
| 2004/0211416 A1 | 10/2004 | Lurie | |
| 2004/0211417 A1 | 10/2004 | Lurie | |
| 2004/0231664 A1 | 11/2004 | Lurie | |
| 2005/0126567 A1 | 6/2005 | Lurie et al. | |
| 2005/0165334 A1 | 7/2005 | Lurie et al. | |
| 2005/0199237 A1 | 9/2005 | Lurie et al. | |
| 2005/0217677 A1 | 10/2005 | Lurie | |
| 2005/0267381 A1 | 12/2005 | Benditt | |

FOREIGN PATENT DOCUMENTS

| | | |
|---|---|---|
| CA | 2077608 A1 | 3/1993 |
| DE | 24 53 490 A1 | 5/1975 |
| EP | 0 029 352 A1 | 5/1981 |

| | | | |
|---|---|---|---|
| EP | 0 139 363 A1 | 5/1985 | |
| EP | 0 245 142 A1 | 11/1987 | |
| EP | 0 367 285 B1 | 5/1990 | |
| EP | 0 411 714 A1 | 2/1991 | |
| EP | 0 509 773 A1 | 10/1992 | |
| GB | 1 465 127 | 2/1977 | |
| GB | 2 139 099 A | 11/1984 | |
| WO | WO90/05518 A1 | 5/1990 | |
| WO | WO93/21982 A1 | 11/1993 | |
| WO | WO94/26229 A1 | 11/1994 | |
| WO | WO95/13108 A1 | 5/1995 | |
| WO | WO95/28193 A1 | 10/1995 | |
| WO | WO96/28215 A1 | 9/1996 | |
| WO | WO99/63926 A1 | 12/1999 | |
| WO | WO01/70332 A1 | 9/2001 | |
| WO | WO02/09216 A1 | 11/2002 | |

OTHER PUBLICATIONS

Cohen, Todd J. et al., "Active Compression-Decompression Resuscitation: a Novel Method of Cardiopulmonary Resuscitation", Department of Medicine and the Cardiovascular Research Institute, UC San Francisco, American Heart Journal 126(5):1145-1150, 1992.
Cohen, Todd J. et al., "Active Compression-Decompression: A New Method of Cardiopulmonary Resuscitation", JAMA 267(21): 2916-2923 (Jun. 3, 1992).
Ambu International A/S "Directions for use of Ambu® CardioPump™", 8 pages.
Dupuis, Yvon G., *Ventilators—Theory and Clinical Application*, pp. 447-448, 481, 496; Jan. 1986, Mosby Company.
Geddes, L.A. et al., "Inspiration Produced by Bilateral Electromagnetic, Cervical Phrenic Nerve Stimulation in Man," IEEE Transactions on Biomedical Engineering 38(9): 1047-1048 (Oct. 1991).
Geddes, L.A. et al., "Optimum Stimulus Frequency for Containing the Inspiratory Muscles with chest Surface Electrodes to Produce Artificial respiration," Annals of Biomedical Engineering 18:103-108 (1990).
Geddes, L.A., "Electrically Produced Artificial Ventilation," Medical Instrumentation 22(5): 263-271 (1988).
Geddes, L.A., "Electroventilation—A Missed Opportunity?", Biomedical Instrumentation & Technology, Jul./Aug. 1998, pp. 401-414.
Glenn, William W.L. et al., "Diaphragm Pacing by Electrical Stimulation of the Phrenic Nerve," Neurosurgery 17(6): 974-984 (1985).
Glenn, William W.L., et al., "Twenty Years of Experience in Phrenic Nerve Stimulation to Pace the Diaphragm," Pace 9: 780-784 (Nov./Dec. 1986, Part I).
Kotze, P.L. et al., "Diaphragm Pacing in the Treatment of Ventilatory Failure,"San. Deel 68:223-224 (Aug. 17, 1995).
Laghi, Franco et al., "Comparison of Magnetic and Electrical Phrenic Nerve Stimulation in assessment of Diaphragmantic Contractility," American Physiological society, pp. 1731-1742 (1996).
Lindner, Karl H. et al., "Effects of Active Compression-Decompression Resuscitation on Myocardial and Cerebral Blood Flow in Pigs" Department of Anerthesiology and Critical Care Medicine, University of Ulm, Germany, Circulation 88(3):1254-1263, (Oct. 7, 1993).
Lurie, Keith G. et al., "Regulated to Death: The Matter of Informed Consent for Human Experimentation in Emergency Resuscitation Research," Cardiac Arrhythmia Center at the University of Minnesota, PACE 18:1443-1447 (Jul. 1995).
Mushin W. W. et al., "Automatic Ventilation of the Lungs—The Lewis-Leigh Inflating Valve," Blackwell Scientific, Oxford, GB, p. 838.
US 5,584,866, 12/1996, Kroll et al. (withdrawn)

* cited by examiner

POSITIVE PRESSURE SYSTEMS AND METHODS FOR INCREASING BLOOD PRESSURE AND CIRCULATION

CROSS REFERENCE TO RELATED APPLICATIONS

This application is a continuation in part application of U.S. patent application Ser. No. 10/796,875, filed Mar. 8, 2004. This application is also a continuation in part application of U.S. patent application Ser. No. 10/660,462, filed Sep. 11, 2003 (now U.S. Pat. No. 7,082,945), which is a continuation in part application of U.S. patent application Ser. No. 10/460,558, filed Jun. 11, 2003 (now U.S. Pat. No. 7,185,649), which is a continuation-in-part of U.S. patent application Ser. No. 10/426,161, filed Apr. 28, 2003 (now U.S. Pat. No. 7,195,012), the complete disclosures of which are herein incorporated by reference.

This application is also related to U.S. patent application Ser. No. 10/765,318, filed Jan. 26, 2004 (now U.S. Pat. No. 7,195,013), the complete disclosure of which is herein incorporated by reference.

This application is also related to U.S. patent application Ser. No. 10/765,318, filed Jan. 26, 2004, (now U.S. Pat. No. 7,195,015), the complete disclosure of which is herein incorporated by reference.

BACKGROUND OF THE INVENTION

This invention relates generally to the field of systemic, intracranial and intraocular pressures. More specifically, the invention relates to devices and methods for decreasing intracranial and intraocular pressures and increasing systemic arterial pressures and systemic vital organ perfusion, such as those resulting from a traumatic head injury, blood loss, and other injuries and illnesses that cause low blood pressure and poor circulation. The invention provides a means to maintain adequate blood pressure and ventilation in a patient who has low blood pressure and is unable to breathe independently in order to maintain vital organ perfusion and oxygenation.

Decreased organ perfusion results in cell death. Both low systemic pressures, or in the case of the brain, high intracranial pressures reduce vital organ perfusion. Hence, head trauma and shock are generally regarded as the leading cause of morbidity and mortality in the United States for children and young adults. Head trauma often results in swelling of the brain. Because the skull cannot expand, the increased pressures within the brain can lead to death or serious brain injury. While a number of therapies have been evaluated in order to reduce brain swelling, including use of hyperventilation and steroids, an effective way to treat intracranial pressures remains an important medical challenge. Similarly, low blood pressure and multi-organ injury decrease vital organ perfusion and when associated with head trauma there is an increase in pressure within the brain and a subsequent decrease in cerebral blood flow. These patients have an extremely high mortality rate and similarly remain a major medical challenge.

BRIEF SUMMARY OF THE INVENTION

In one embodiment, the invention provides a device for decreasing intracranial or intraocular pressures and increasing systemic blood pressures and organ perfusion. The device comprises a housing having an inlet opening and an outlet opening that is adapted to be interfaced with a person's airway. The device further includes a valve system that is operable to regulate respiratory gas flows through the housing and into the person's lungs during spontaneous or artificial inspiration. For a person who requires artificial inspiration, the valve system can be attached to a vacuum source. The valve system assists in lowering intrathoracic pressures during spontaneous inspiration and in non-breathing patients when not actively delivering a breath to in turn lower intracranial pressures or intraocular pressures and increase systemic perfusion pressures. The valve system may also be used to continuously or intermittently lower pressures in the head by lowering the pressures within the thorax. In addition, the invention lowers the pressures within the left and right heart, when positive pressure ventilations are not being provided. The reduced pressures in the thorax, including the heart, draws more blood back to the heart thereby helping to increase the efficiency of heart function and cardiac output. The invention can therefore be used to treat patients suffering from a number of disease states including but not limited to those suffering from elevated intracranial pressures, intraocular pressures, shock, hypotension, circulatory collapse, cardiac arrest, those in dialysis and heart failure. The invention is based upon the discovery that reductions in intrathoracic pressure result in a decrease in intracranial pressures and enhancement of blood flow to the heart.

Such a device may also be used to facilitate movement of cerebral spinal fluid. In so doing, intracranial pressures may be further reduced. Such a device may therefore be used to treat those suffering from head trauma associated with elevated intracranial pressures as well as those suffering from conditions that cause low systemic blood pressure.

In one aspect, the valve system is configured to open to permit respiratory gasses to freely flow to the person's lungs during spontaneous respirations when the negative intrathoracic pressure reaches a pressure in the range from about −2 cmH2O to about −20 cmH2O in order to reduce intrathoracic pressure and thus reduce intracranial or intraocular pressures. In this way, the negative intrathoracic pressure is lowered until a threshold pressure is reached, at which time the valve opens. The cycle may be repeated continuously or periodically to repetitively lower intrathoracic pressures. In another aspect, the valve system is configured to generate an intrathoracic vacuum in the range from about −2 cm H2O to about −20 cm H2O in order to both reduce intrathoracic pressure and thus reduce intracranial or intraocular pressures and to enhance blood flow to the heart. The device may include means for repetitively compressing the chest to improve blood circulation in patents in or with low blood circulation or cardiac arrest. The compression could be accomplished with an automated chest compression, a circumferential vest, and the like. This would improve blood flow to the heart and brain in patients with low blood circulation. When the device compresses the chest blood is forced out of the heart to increase perfusion of the vital organs. When the compression means is released, blood flows back into the heart. In some cases, a decompression device could also be used to actively lift or decompress the chest to enhance the blood flow back to the heart.

The device may also include means for causing the person to artificially inspire through the valve system. For example, the device may utilize an electrode, an iron lung cuirass device, a chest lifting device, a ventilator or the like. By reducing the pressure within the chest, respiratory gases flow into the lungs and provide oxygen. By sequentially compressing the chest and then decompressing the chest, the chest is turned into a bellows and blood is circulated and respiratory gases are exchanged. This action can be timed with the natural contractions of the heart, such as by using an ECG. In one embodiment, the chest is compressed and then the chest is allowed to recoil to its resting position to circulate blood and respiratory gases. After each chest wall recoil, a device is used to lower intrathoracic pressures to create an intrathoracic vacuum to enhance blood flow back to the heart. In another embodiment, the chest is compressed and then actively decompressed to circulate blood and respiratory gases, and after each chest decompression a device is used to lower intrathoracic pressures to create an intrathoracic vacuum to enhance blood flow back to the heart and also lower intracranial pressures. Devices that may be used to lower intrathoracic pressures include any type of vacuum, including those incorporated into a ventilator. During at least some of the decompressions, respiratory gases may be permitted to freely flow to the lungs to provide proper ventilation.

In another embodiment, the device may comprise a means to reduce intrathoracic pressure by applying a vacuum within the airway. The vacuum may be adjusted in terms of frequency, amplitude, and duration. This results in a decrease in intracranial pressure in proportion to the degree of vacuum applied. Hence, intracranial pressures may be reduced simply by manipulating airway pressures to reduce intrathoracic pressures. In addition, the vacuum created within the thorax enhances blood flow back to the heart, thereby simultaneously increasing cardiac output and systemic vital organ perfusion. Such a vacuum may be generated from an external vacuum source, through the airway or a chest tube between the ribs, or it may be generated using a ventilator capable of applying a negative pressure.

The device may further include a mechanism for varying the level of impedance or resistance of the valve system. It may include adding positive expiratory pressure when the chest is being compressed. This device may be used in combination with at least one physiological sensor that is configured to monitor at least one physiological parameter of the person. In this way, the mechanism for varying the level of impedance intrathoracic pressure may be configured to receive signals from the sensor and to vary the level of impedance of the valve system based on the signals. Examples of sensors that may be used include those that measure respiratory rate, intrathoracic pressure, intratracheal pressure, blood pressure, right heart pressure, heart rate, end tidal CO2, oxygen level, intracranial perfusion, and intracranial pressure.

In one aspect, a coupling mechanism may be used to couple the valve system to the person's airway. Examples of coupling mechanisms include a mouthpiece, an endotracheal tube, and a face mask.

A wide variety of valve systems may be used to repetitively decrease the person's intrathoracic pressure. For example, valve systems that may be used include those having spring-biased devices, those having automated, electronic or mechanical systems to occlude and open a valve lumen, duck bill valves, ball valves, other pressure sensitive valve systems capable of opening a closing when subjected to low pressure differentials triggered either by spontaneous breathing and/or external systems to manipulate intrathoracic pressures (such as ventilators, phrenic nerve stimulators, iron lungs, and the like).

In another embodiment, the invention provides a method for decreasing intracranial or intraocular pressures. According to the method, a valve system is coupled to a person's airway and is configured to at least periodically reduce or prevent respiratory gases from flowing to the person's lungs. With the valve system coupled to the airway, the person's negative intrathoracic pressure is repetitively decreased to in turn repetitively lower pressures in the venous blood vessels that transport blood out of the head. In so doing, intracranial and intraocular pressures are reduced. Such a method also facilitates movement of cerebral spinal fluid. In so doing, intracranial pressures are further reduced. As such, this method may also be used to treat a person suffering from head trauma that is associated with elevated intracranial pressures, those suffering from heart conditions that increase intracranial pressures, such as atrial fibrillation and heart failure, and those suffering from low blood pressure that is caused in part or whole by a decrease in cardiac output or function.

The person's negative intrathoracic pressure may be repetitively decreased as the person repeatedly inspires through the valve system. This may be done by the person's own efforts (referred to as spontaneous breathing), or by artificially causing the person to repeatedly inspire through the valve system. For example, the person's intrathoracic pressure can be lowered by repeatedly stimulating the phrenic nerve, by manipulating the chest with an iron lung cuirass device, by generating negative pressures within the thorax using a ventilator, by applying a vacuum within the thorax that can be regulated by the valve system, by applying a high frequency ventilator that supplies oscillations at a rate of about 200 to about 2000 per minute, or the like. Lowering the intrathoracic pressure can be used to draw respiratory gases into the lungs, draw more blood back to the heart, or both. Lowering the intrathoracic pressure can also be used to lower intracranial and intraocular pressures.

In another aspect, the level of impedance of the valve system may be fixed or variable. If variable, at least one physiological parameters of the person may be measured, and the impedance level may be varied based on the measured parameters.

To couple the valve system to the airway, a variety of techniques may be used, such as by using a mouthpiece, an endotracheal tube, a face mask or the like. Further, the respiratory gases may be prevented from entering the lungs through the valve system until a negative intrathoracic pressure in the range from about 0 cmH2O to about −25 cmH2O is achieved, at which time the valve system permits respiratory gases to flow to the lungs.

In another embodiment, the invention provides a method for treating a person suffering from head trauma associated with elevated intracranial pressures. According to the method, a positive pressure breath is delivered to the person. Respiratory gases are extracted from the person's airway by a vacuum source attached to a device situated between the ventilator and the person's airway to create an intrathoracic vacuum. In turn, this reduces intracranial pressures and may also lower pressures in the venous blood vessels that transport blood out of the head. In some options positive pressure breaths are delivered to the lungs to provide respiratory gases. The steps of delivering positive pressure breaths and extracting respiratory gases are repeated to continue the treatment. Further, a positive pressure breath need not be provided every time before extracting gases, but only when needed to provide proper ventilation. In some cases, blood volume may be reduced by the use of diuretics or other means including but not limited to intentional blood loss or volume depletion to enhance the effects of lowering intracranial pressures by lowering intrathoracic pressures.

In some options, the patient may also have his or her intrathoracic pressures externally manipulated with an external thoracic positive pressure source while being provided with the positive pressure breaths and the extraction of gases from the airway. Examples of external thoracic positive pressure sources include a mechanical extrathoracic vest, a body cuirass, a compression piston, a compression cup and the like. These devices may be supplied with energy from a variety of sources, such as pneumatic, electric, combustion and the like. Further, the external compressions may be timed with cardiac activity, e.g., with ECG activity. Further, the external compressions and/or application of the positive pressure breath and the vacuum may be used in combination with invasive means to maintain blood pressure, such as by removing blood from the patient. Also, in some cases, the patient's chest may also need to at least periodically be decompressed. In such cases, a valve may be placed in the patient's airway to prevent air from rushing into the patient's lungs for at least some time in order to increase the magnitude of the negative intrathoracic pressure that is created.

In one aspect, the delivery of the positive pressure breaths and the extraction of gases are performed using a mechanical ventilator. The respiratory gases may be extracted with a constant extraction or a pulsed extraction.

In a further aspect, the breath may be delivered for a time in the range for about 250 milliseconds to about 2 seconds. Also, the breath may be delivered at a rate in the range from about 0.1 liters per second to about 5 liters per second. In another aspect, the vacuum may be maintained at a pressure in the level from about 0 mmHg to about −50 mmHg. The vacuum may be maintained with a negative flow or without any flow. The time that the positive pressure breath is supplied relative to the time in which respiratory gases are extracted may be in the range from about 0.5 to about 0.1.

A variety of equipment may be used to extract the respiratory gases including mechanical ventilators, phrenic nerve stimulators, ventilator bags, a vacuum attached to the airway device, iron lung cuirass devices, a chest tube, and the like. In some cases, a threshold valve may also be coupled to the person's airway. The threshold valve may be configured to open when an adult's negative intrathoracic pressure exceeds about −3 cmH2O. For pediatric cases, the valve may open when the pressure exceeds about −2 cmH2O to about −5 cmH2O. In this way, when the person inhales, the negative intrathoracic pressure may be lowered.

A variety of schemes may be used to deliver and extract respiratory gases. For example, respiratory gases may be extracted to achieve a pressure of about −5 mmHg to about −10 mmHg and then kept generally constant until the next positive pressure breath. As another example, the positive breath may be slowly delivered and the intrathoracic pressure may be rapidly lowered to a pressure of about −10 mmHg to about −20 mmHg and then gradually increased towards about 0 mmHg. As a further example, the intrathoracic pressure may be slowly lowered to a pressure of about −20 mm Hg.

In a further embodiment, the invention provides a device for lowering intrathoracic pressures. The device comprises a housing having an interface that is adapted to couple the housing to the person's airway. A vacuum source is in fluid communication with the housing for repeatedly extracting respiratory gases from the person's lungs and airway to create and periodically maintain a negative intrathoracic pressure. A vacuum regulator is used to regulate the extraction of respiratory gases from the patient's lungs and airway. Also, a positive pressure source is in fluid communication with the housing for intermittently supplying positive pressure breaths to the person if needed. Such a device may be used to treat a variety of ailments, such as head trauma associated with elevated intracranial pressures, low blood pressure, low blood circulation, low blood volume, cardiac arrest and heart failure.

In some cases, a switching mechanism may be used to stop the extraction of respiratory gases or to deliver of a positive pressure breath. A variety of switching mechanisms may be used, such as mechanical devices, magnetic devices, and electronic devices. Also, a variety of vacuum sources may be used to extract the respiratory gases, including a mechanical ventilator, a vacuum with vacuum regulator, a phrenic nerve stimulator, an extrathoracic vest, a ventilator bag, and an iron lung cuirass device, a suction line, a venturi device attached to an oxygen tank and the like.

To regulate the vacuum, a threshold valve may be placed in fluid communication with the person's airway. The threshold valve may be configured to open when the person's negative intrathoracic pressure reaches about −3 cm H2O to about −20 cm H2O to permit respiratory gases to flow into the person's airway. Also, a variety of pressure sources may be used to deliver a positive pressure breath, such as a mechanical ventilator, a hand held bag valve resuscitator, mouth-to-mouth, or a means to provide intermittent positive pressure ventilation. A variety of gauges may be incorporated into the device that are coupled to sensors to measure, for example, the vacuum pressure applied to the patient and other physiological measures such as the intratracheal pressure or intracranial pressure.

In one specific aspect, the invention provides methods and devices that allow the chest to be compressed and decompressed, akin to transforming the chest into a bellows. A wide variety of devices or systems may be used to compress and decompress the chest as described herein. Further, an impedance valve and/or intrathoracic vacuum regulator may be used to lower intrathoracic pressures within the chest when not actively compressing or decompressing the chest to enhance blood flow black to the heart and lower intracranial pressures. Optionally, the device may have the capability to provide periodic positive pressure ventilations. In one particular option, the compressions may be timed with the heart beat, such as by using an ECG. Also, the decompressions could happened less often than after every compression. For example, the chest may be decompressed about 6 to about 30 times a minute to provide proper negative pressure ventilations, i.e., the creation of a vacuum within the thoracic to naturally inspire air through an unimpeded airway, such as by the use of an iron lung, phrenic nerve stimulation, a suction cup adhered to the chest, and the like. Such a device thus provides a way to artificially maintain blood pressure and ventilation, by negative pressure ventilation and/or by positive pressure ventilations. The device also enhances vital organ circulation and lowers intracranial pressures in patients with low blood pressure who may or may not be able to breathe as well.

DETAILED DESCRIPTION OF THE INVENTION

Figure 1:
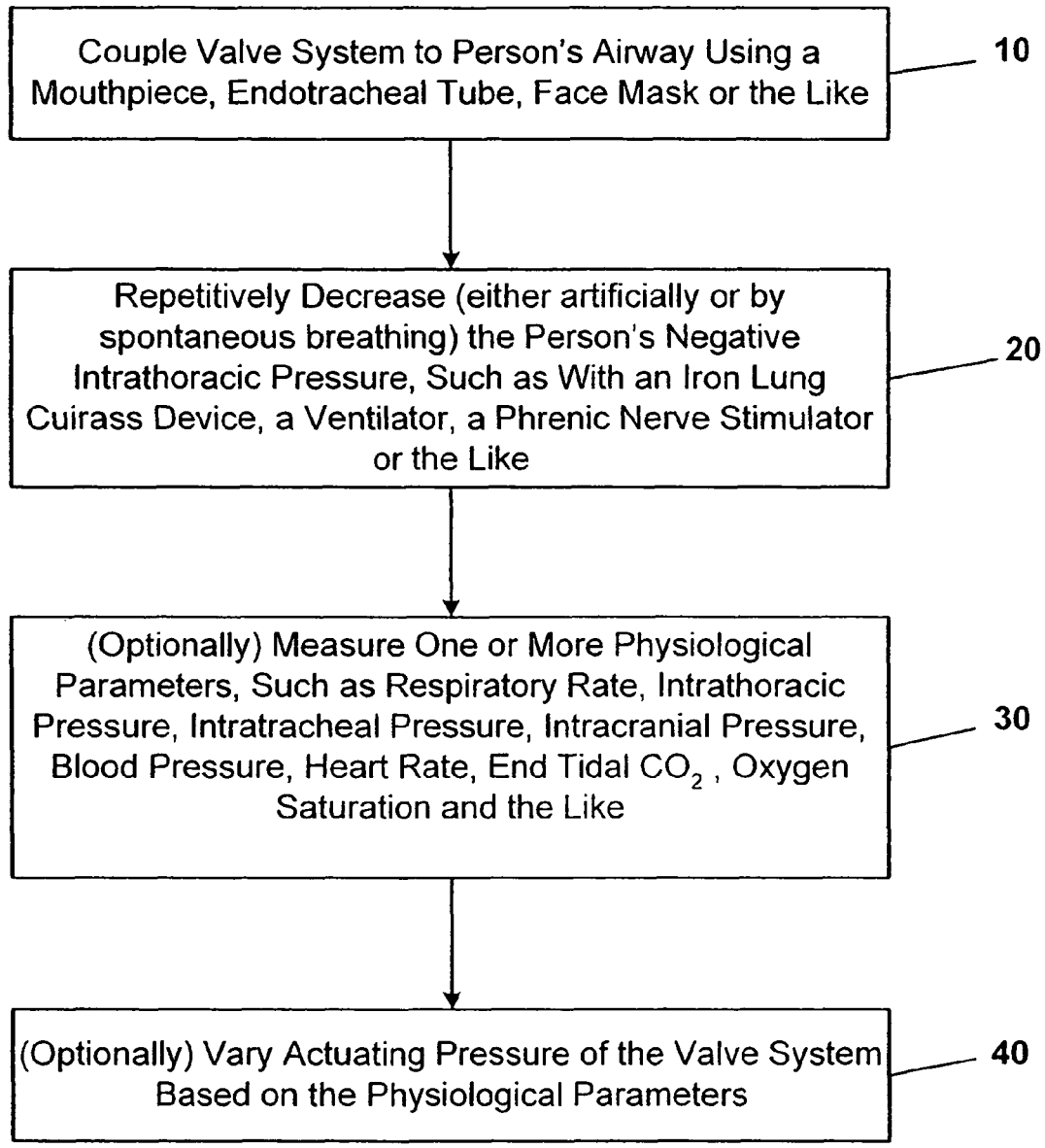
FIG. 1 is a flow chart illustrating one method for reducing intracranial and intraocular pressures according to the invention.

In a broad sense, the invention provides devices and techniques for lowering intracranial and intraocular pressures and increasing cerebral perfusion pressures. Such devices and techniques may be particularly helpful with patients who have suffered a traumatic brain injury and those with low blood flow states and low blood pressure. Examples of conditions that may be treated include hypotension, shock secondary to hypovolemia, sepsis, heart failure, and the like. One way to lower the pressure within the head but maintain or increase systemic pressures is by using a valve system that is coupled to a person's airway and that is used to lower intrathoracic pressures. In so doing, the valve systems may be used to accelerate the removal of venous blood from the brain, thereby decreasing intracranial and intraocular pressures. At the same time, the systemic pressures increase due to enhancement of venous return to the heart. Other techniques may be used as well, such as by creating a vacuum intermittently within the thorax and/or by repeatedly compressing and/or decompressing the patient's chest using an external thoracic positive pressure source. By reducing intracranial pressures, movement of cerebral spinal fluid is also enhanced. In so doing, intracranial pressures are further reduced thereby providing further treatment for those suffering from head trauma. In some cases, the valve systems may also be used to treat the brain function in a person suffering from a heart condition (atrial fibrillation, heart failure, cardiac tamponade, and the like) that results in elevated intracranial pressures. Such heart conditions may include, for example, atrial fibrillation or heart failure. By reducing intracranial pressures, cerebral spinal fluid movement and translocation is increased to help improve brain function.

Intracranial pressures are regulated by the amount the cerebral perfusion pressure, which is determined by the arterial blood pressure to the head, the pressures within the skull, and the pressures within the venous system that drains blood flow from the brain. The devices and methods of the invention may be used to enhance the egress of venous blood out of the brain, thereby lowering intracranial pressures. The devices and methods can be used in patients that are breathing spontaneously and those that require assisted ventilation. To do so, the devices and methods may be used to augment the intrathoracic vacuum effect each time a patient inhales (or in the case of a non-breathing patient, each time the pressure within the chest is manipulated to fall below atmospheric pressure), thereby lowering the pressures in the thorax and in the venous blood vessels that transport blood out of the brain. The vacuum effect is transduced back into the brain, and as a result, intracranial pressures are lowered with each inspiratory effort. This in turn causes more venous blood to flow out of the head than would otherwise be possible, resulting in lower intracranial pressures and lower intraocular pressures. In addition, circulation to the vital organs is increased as the increase in venous return to the heart each time a negative intrathoracic pressure is generated results in an increase in cardiac output and improved vital organ perfusion. As such, this invention may be used to help patients suffering from low cardiac output states and low blood pressure.

To prevent or impede respiratory gases from flowing to the lungs, a variety of impeding or preventing mechanisms may be used, including those described in U.S. Pat. Nos. 5,551, 420; 5,692,498; 6,062,219; 5,730,122; 6,155,257; 6,234,916 and 6,224,562, and in U.S. patent application Ser. No. 10/224, 263, filed on Aug. 19, 2002 ("Systems and Methods for Enhancing Blood Circulation"), Ser. No. 10/401,493, filed Mar. 28, 2003 ("Diabetes Treatment Systems and Methods"), Ser. No. 09/966,945, filed Sep. 28, 2001 and Ser. No. 09/967, 029, filed Sep. 28, 2001, the complete disclosures of which are herein incorporated by reference. The valve systems may be configured to completely prevent or provide resistance to the inflow of respiratory gases into the patient while the patient inspires. For valve systems that completely prevent the flow of respiratory gases, such valves may be configured as pressure responsive valves that open after a threshold negative intrathoracic pressure has been reached.

For example, the resistance to the inflow of respiratory gases may be set between about 0 cm H2O and about −25 cm H2O and may be variable or fixed. More preferably, the valve system may be configured to open when the negative intrathoracic pressure is in the range from about −2 cmH2O to about −20 cmH2O. In addition, the valve system may used continuously or on a variable basis. For example, the valve system may be used for every other spontaneous breath.

Although not intended to be limiting, specific kinds of impedance valves that may be used to reduce intracranial and intraocular pressures include those having spring-biased devices, automated/electronic and mechanical means to occlude and open a valve lumen, duck bill valves, ball valves, and other pressure sensitive valve systems capable of opening and closing when subjected to low pressure differentials triggered either by spontaneous breathing and/or external means to manipulate intrathoracic pressure (such as ventilators, phrenic nerve stimulators, an iron lung, and the like).

In the past, such threshold valve systems have been used to increase the venous preload on the heart and to increase cardiac output, stroke volume and blood pressure because of the augmented effects of the intrathoracic vacuum on the subsequent cardiac contraction. In contrast, the techniques of the invention function by facilitating the removal of blood from the venous side of the brain. Although there may be an increase in blood flow out of the heart to the vital organs (including to the brain) when using such valve systems, the effect of the valve systems on lowering of intracranial pressures was quite unexpected because of the known increase in blood flow to the brain. Remarkably, however, the reduction of venous blood pressures from the brain remains substantial when using the valve systems. Thus, despite the increase in blood flow to the brain, the net effect of the valve system is a decrease in intracranial pressures.

With the valve system coupled to the person's airway, the negative intrathoracic pressure may be enhanced by inspiring through the valve system. If the person is spontaneously breathing, the person may simply breath through the valve system. If the person is not breathing, artificial inspiration may be induced using a variety of techniques, including electrical stimulation of the diaphragm, a negative pressure ventilator such as a body cuirass or iron lung, or a positive pressure ventilator capable of also generating a vacuum between positive pressure ventilations. As one example, at least some of the respiratory muscles, and particularly the inspiratory muscles, may be stimulated to contract in a repeating manner in order to cause the person to inspire through the valve system, thereby increasing the magnitude and prolonging the duration of negative intrathoracic pressure, i.e., respiratory muscle stimulation increases the duration and degree that the intrathoracic pressure is below or negative with respect to the pressure in the peripheral venous vasculature. Upon contraction of the respiratory muscles, the patient will typically "gasp". These techniques may be performed alone, or in combination with a valve system.

Among the respiratory muscles that may be stimulated to contract are the diaphragm, the chest wall muscles, including the intercostal muscles and the abdominal muscles. Specific chest wall muscles that may be stimulated to contract include those that elevate the upper ribs, including the scaleni and sternocleidomastoid muscles, those that act to fix the shoulder girdle, including the trapezii, rhomboidei, and levatores angulorum scapulorum muscles, and those that act to elevate the ribs, including the serrati antici majores, and the pectorales majores and minores as described generally in Leslie A. Geddes, "Electroventilation—A Missed Opportunity?", Biomedical Instrumentation & Technology, July/August 1998, pp. 401-414, the complete disclosure of which is herein incorporated by reference. Of the respiratory muscles, the two hemidiaphragms and intercostal muscles appear to be the greatest contributors to inspiration and expiration. The respiratory muscles may be stimulated to contract in a variety of ways. For example, the diaphragm may be stimulated to contract by supplying electrical current or a magnetic field to various nerves or muscle bundles which when stimulated cause the diaphragm to contract. Similar techniques may be used to stimulate the chest wall muscles to contract. A variety of pulse trains, pulse widths, pulse frequencies and pulse waveforms may be used for stimulation. Further, the electrode location and timing of pulse delivery may be varied. In one particular aspect, an electrical current gradient or a magnetic field is provided to directly or indirectly stimulate the phrenic nerve.

To electrically stimulate the inspiratory motor nerves, electrodes are preferably placed on the lateral surface of the neck over the point where the phrenic nerve, on the chest surface just lateral to the lower sternum to deliver current to the phrenic nerves just as they enter the diaphragm, on the upper chest just anterior to the axillae to stimulate the thoracic nerves, in the oral pharyngeal region of the throat, or on the larynx itself. However, it will be appreciated that other electrode sites may be employed. For example, in one embodiment the respiratory muscles are stimulated by a transcutaneous electrical impulse delivered along the lower antero-lat margin of the rib cage. In one embodiment, inspiration is induced by stimulating inspiratory muscles using one or more electrodes attached to an endotracheal tube or pharyngeal tube. To stimulate the diaphragm, the phrenic nerve may be stimulated in the neck region near C3-C7, such as between C3, C4 or C5, or where the phrenic nerves enter the diaphragm. Alternative techniques for stimulating diaphragmatic contraction include magnetic field stimulation of the diaphragm or the phrenic nerve. Magnetic field stimulation may also be employed to stimulate the chest wall muscles. Electrical field stimulation of the diaphragm or the chest wall muscles may be accomplished by placing one or more electrodes on the skin, preferably in the vicinity of the neck or the lower rib cage (although other locations may be employed) and then providing an electrical voltage gradient between electrodes that induces transcutaneous current flow to stimulate the respiratory muscles to contract. Still further, subcutaneous electrodes may also be used to stimulate respiratory muscle contraction. Other techniques are described in U.S. Pat. No. 6,463,327, the complete disclosure of which is herein incorporated by reference.

The valve systems may have a fixed actuating pressure or may be variable so that once a desired negative intrathoracic pressure is reached, the resistance to flow may be lessened. Further, the valves of the invention may be configured to be variable, either manually or automatically. The extent to which the resistance to flow is varied may be based on physiological parameters measured by one or more sensors that are associated with the person being treated. As such, the resistance to flow may be varied so that the person's physiological parameters are brought within an acceptable range. If an automated system is used, such sensors may be coupled to a controller which is employed to control one or more mechanisms that vary the resistance or actuating pressure of the inflow valve as generally described in the references that have been incorporated by reference.

Hence, the valve systems of the invention may also incorporate or be associated with sensors that are used to detect changes in intrathoracic pressures or other physiological parameters. In one aspect, the sensors may be configured to wirelessly transmit their measured signals to a remote receiver that is in communication with a controller. In turn the controller may use the measured signals to vary operation of the valve systems described or incorporated by reference herein. For example, sensors may be used to sense blood pressure, pressures within the heart, intrathoracic pressures, positive end expiratory pressure, respiratory rate, intracranial pressures, intraocular pressures, respiratory flow, oxygen delivery, temperature, blood pH, end tidal $CO_2$, tissue $CO_2$, blood oxygen, cardiac output or the like. Signals from these sensors may be wirelessly transmitted to a receiver. This information may then be used by a controller to control the actuating pressure or the resistance of an inflow valve as described in the references incorporated herein by reference.

The techniques for reducing intracranial pressures may be used in a variety of settings. For example, the techniques may be used in person's who are spontaneously breathing, those who are not breathing but whose hearts are beating, and those in cardiac arrest. In the latter case, the techniques may use some means to create a vacuum intermittently within the thorax during the performance of CPR. This could be by using a valve system or some other type of pressure manipulation system. Further, such systems may be used in other settings as well, including when the person is breathing.

FIG. 1 is flow diagram illustrating one method for reducing intracranial or intraocular pressures. As shown in step 10, the process proceeds by coupling a valve system to the person's airway. Any kind of coupling mechanism may be used, such as by a mouthpiece, an endotracheal tube, a face mask, or the like. Further, any of the valve systems described or incorporated herein by reference may be used. In step 20, the person's negative intrathoracic pressure is repetitively decreased (either artificially or by spontaneous breathing). Examples of techniques to artificially reduce the negative intrathoracic pressure include use of an iron lung cuirass device, a ventilator that is capable of generating negative pressures, a ventilator that is capable of providing high frequency oscillations at a rate of about 200 to about 2000 per minute, a phrenic nerve stimulator, or the like. As the person's negative intrathoracic pressure is repeatedly decreased while the valve system is coupled to the airway, the pressures in the venous vessels that transport blood out of the head are also lowered. In so doing, intracranial and intraocular pressures are reduced.

As shown in step 30, various physiological parameters of the person may optionally be measured. Examples of such parameters include respiratory rate, intrathoracic pressure, intertracheal pressure, intracranial pressure, intracranial blood flow, intraocular pressure, blood pressure, heart rate, end tidal $CO_2$, oxygen saturation, and the like. Further, as shown in step 40, the valve system's actuating threshold level may optionally be varied based on the measured physiological parameters. This may be done to maximize the amount of blood drawn out of the brain or simply to monitor the patient's condition to insure that the patient remains stable.

Figure 2:
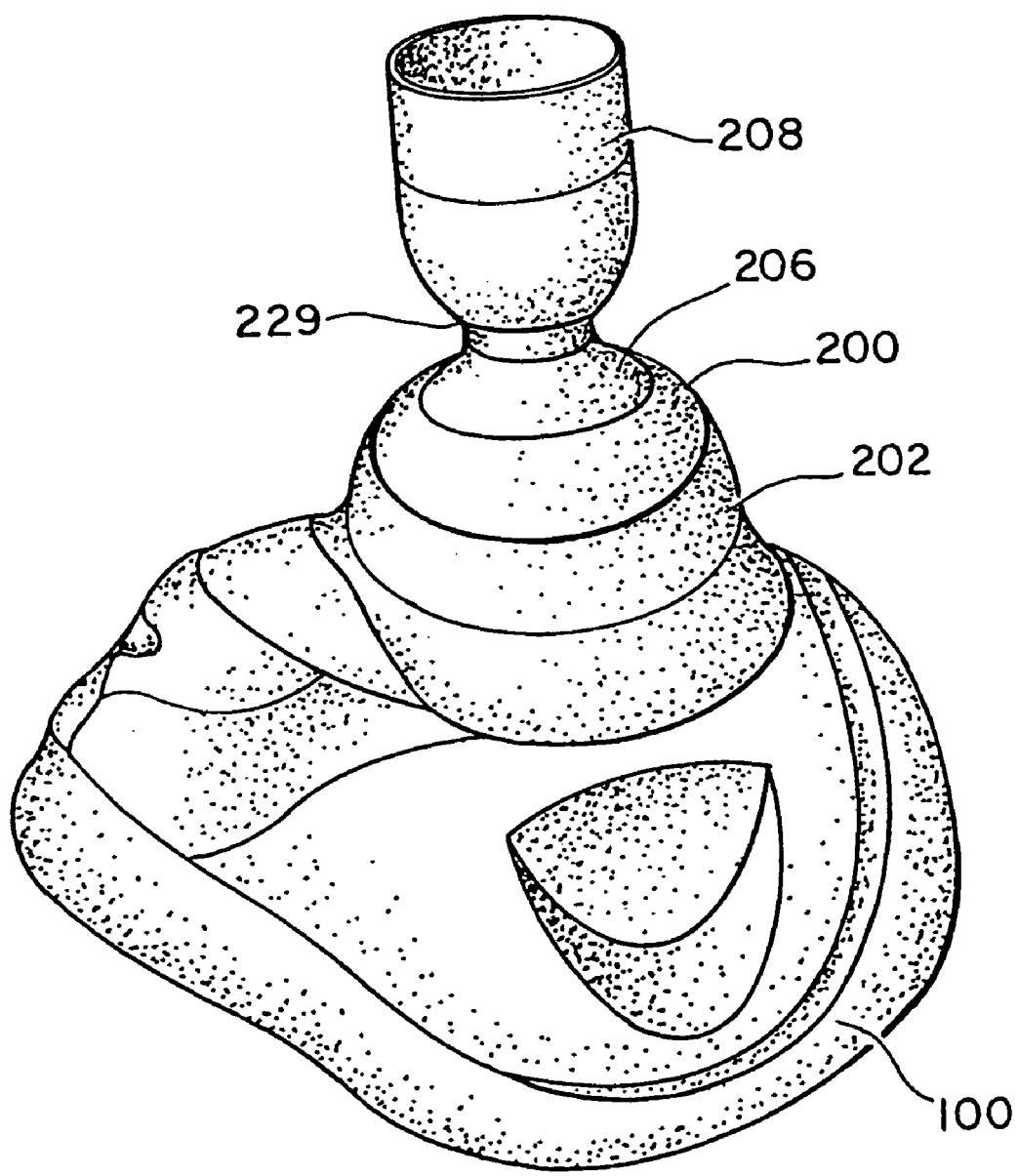
FIG. 2 is a perspective view of one embodiment of a facial mask and a valve system that may be used to reduce intracranial and intraocular pressures according to the invention.

FIG. 2 illustrates one embodiment of a facial mask 100 to which is coupled a valve system 200. Mask 100 is configured to be secured to a patient's face so as to cover the mouth and nose. Mask 100 and valve system 200 are examples of one type of equipment that may be used to lower intrathoracic pressures and thereby lower intracranial and intraocular pressures. However, it will be appreciated that other valve systems and other coupling arrangements may be used including, for example, those previously referenced. As such the invention is not intended to be limited to the specific valve system and mask described below.

Figure 3:
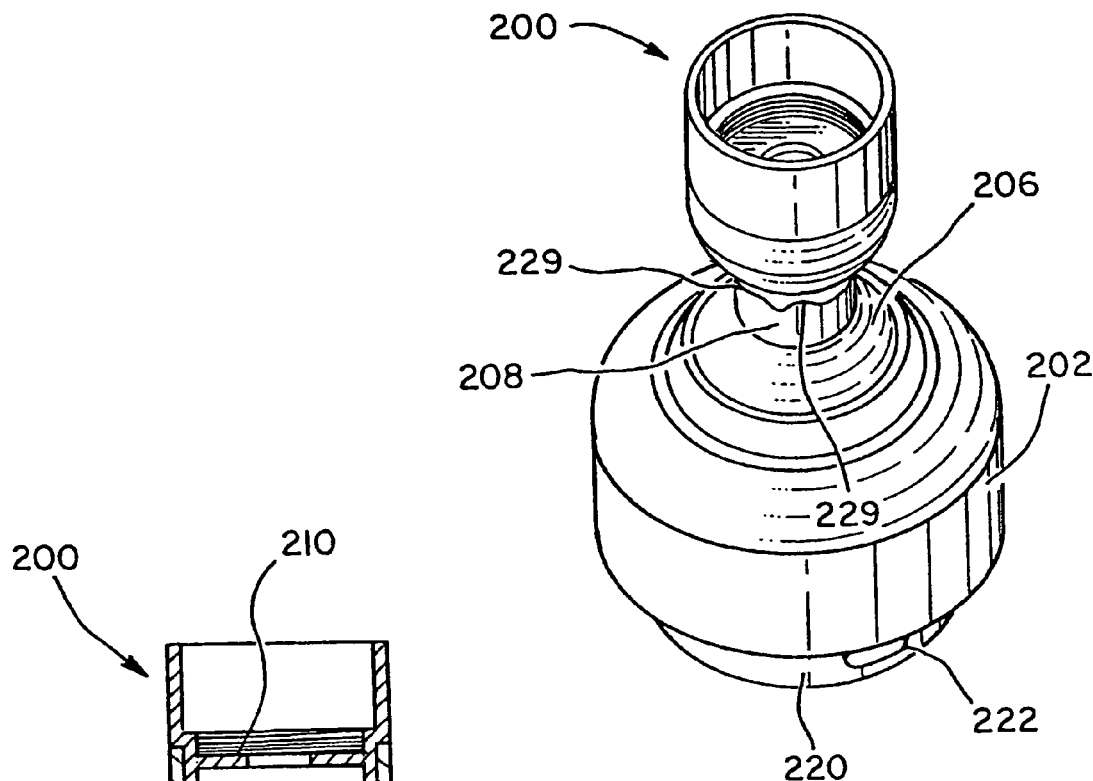
FIG. 3 is a perspective view of the valve system of FIG. 2.
Figure 4:
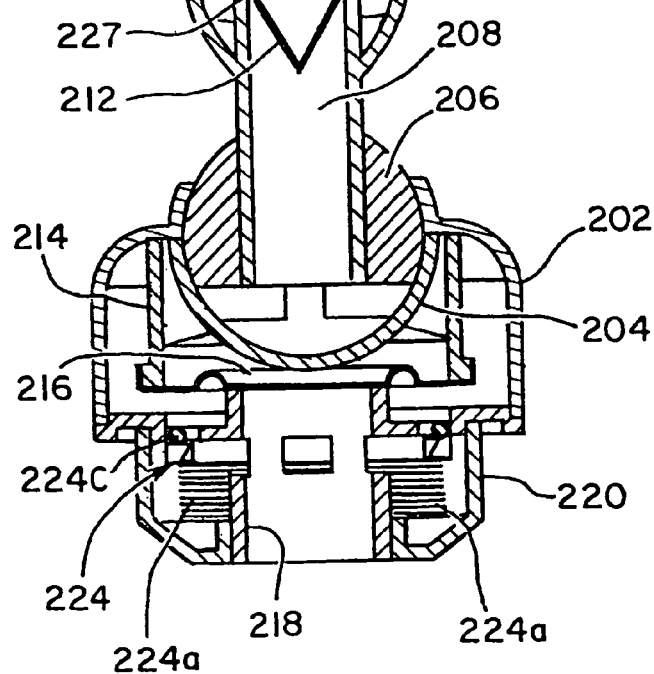
FIG. 4 is a cross sectional side view of the valve system of FIG. 3.
Figure 5:
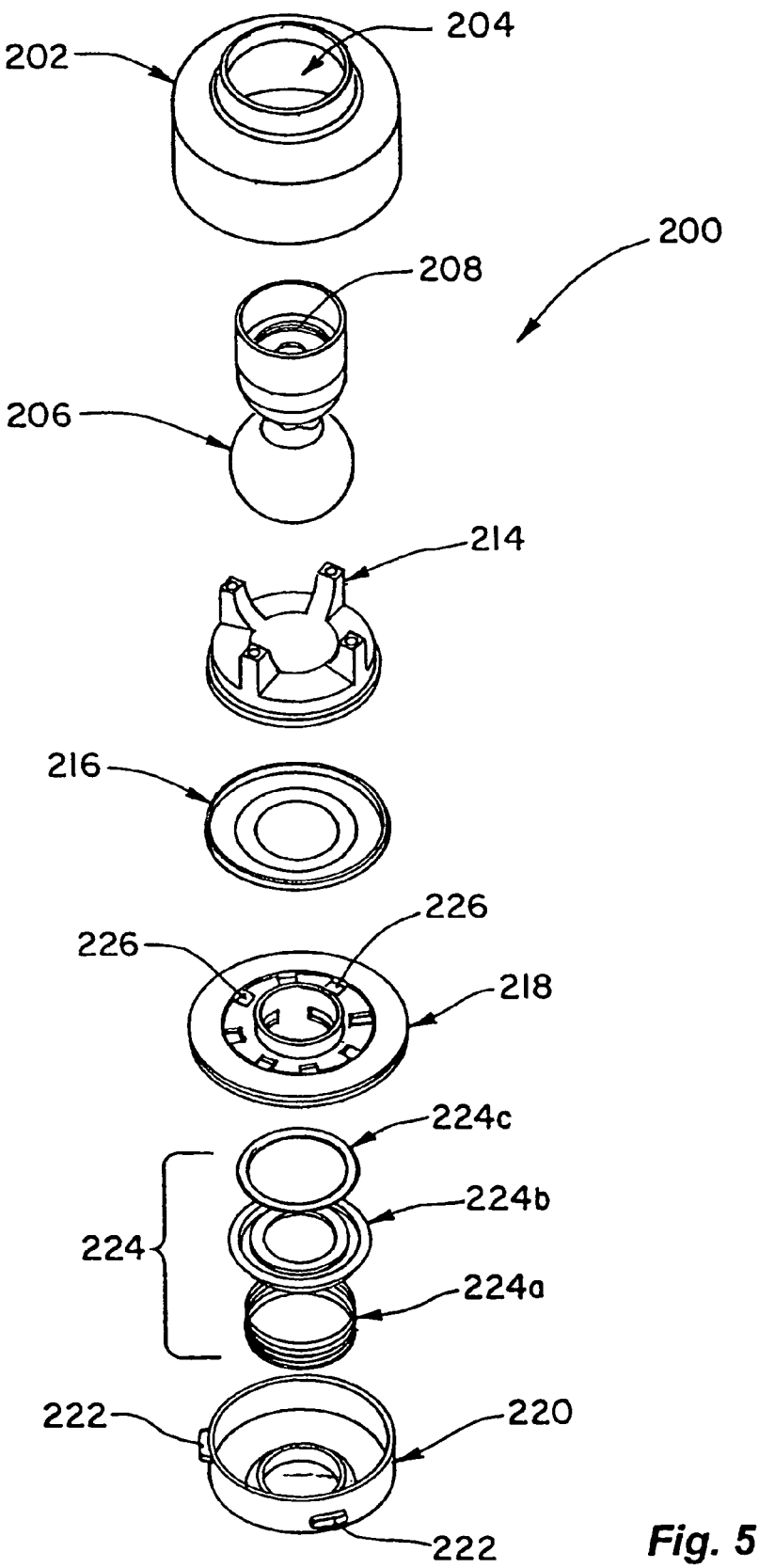
FIG. 5 is an exploded view of the valve system of FIG. 3.

Referring also to FIGS. 3-5, valve system 200 will be described in greater detail. Valve system 200 includes a valve housing 202 with a socket 204 into which a ball 206 of a ventilation tube 208 is received. In this way, ventilation tube 208 may rotate about a horizontal axis and pivot relative to a vertical axis. A respiratory source, such as a ventilation bag, may be coupled to tube 208 to assist in ventilation. Disposed in ventilation tube 208 is a filter 210 that is spaced above a duck bill valve 212. A diaphragm holder 214 that holds a diaphragm 216 is held within housing 202. Valve system 200 further includes a patient port 218 that is held in place by a second housing 220. Housing 220 conveniently includes tabs 222 to facilitate coupling of valve system 200 with facial mask 100. Also held within housing 220 is a check valve 224 that comprises a spring 224a, a ring member 224b, and an o-ring 224c. Spring 224a biases ring member 224b against patient port 218. Patient port 218 includes bypass openings 226 that are covered by o-ring 224c of check valve 224 until the pressure in patient port 218 reaches a threshold negative pressure to cause spring 224a to compress.

When the patient is actively ventilated, respiratory gases are forced through ventilation tube 208. The gases flow through filter 210, through duck bill valve 212, and forces up diaphragm 214 to permit the gases to exit through port 218. Hence, at any time the patient may be ventilated simply by forcing the respiratory gases through tube 208.

During the exhalation phase of a breathing cycle, expired gases flow through port 218 and lift up diaphragm 214. The gases then flow through a passage 227 in ventilation tube 208 where they exit the system through openings 229 (see FIG. 3).

During the inhalation phase of a breathing cycle, valve system 200 prevents respiratory gases from flowing into the lungs until a threshold negative intrathoracic pressure level is exceeded. When this pressure level is exceeded, check valve 224 is pulled downward as springs 224a are compressed to permit respiratory gases to flow through openings 226 and to the patient's lungs by initially passing through tube 208 and duck bill valve 212. Valve 224 may be set to open when the negative intrathoracic pressure is in the range from about 0 cm H2O to about −25 cm H2O, and more preferably from about −2 cm H2O to about −20 cm H2O. Hence, the magnitude and duration of negative intrathoracic pressure may be enhanced during patient inhalation by use of valve system 200. Once the intrathoracic pressure falls below the threshold, recoil spring 224a again close check valve 224. In this way, pressure within the venous blood vessels that transport blood out of the brain are also lowered. In so doing, more blood is drawn out of the brain to reduce intracranial and intraocular pressures.

Figure 6:
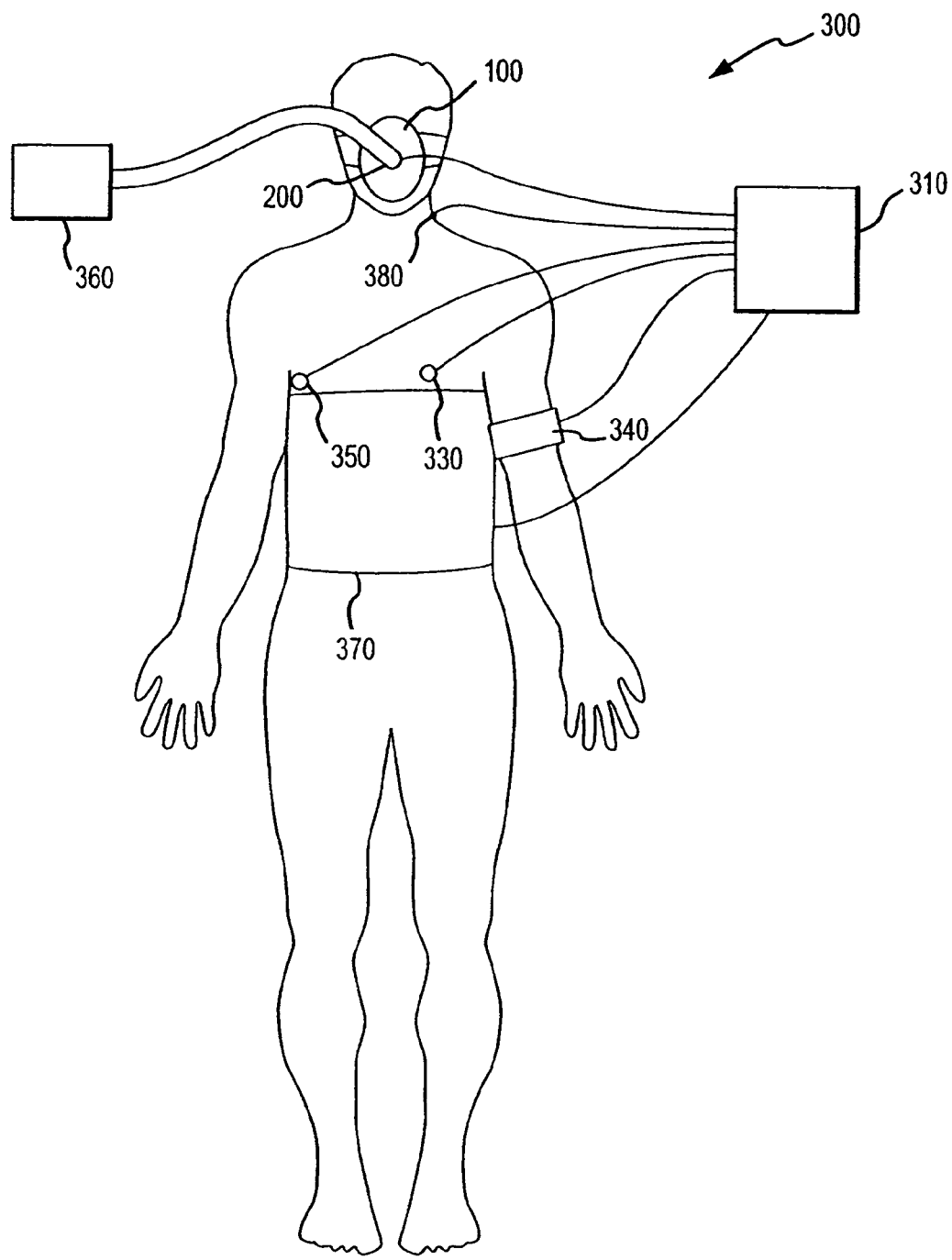
FIG. 6 is a schematic diagram of a system for reducing intracranial and intraocular pressures according to the invention.

Any of the valve systems described herein may be incorporated into a treatment system 300 as illustrated in FIG. 6. System 300 may conveniently include facial mask 100 and valve system 200, although any of the valve systems or interfacing mechanisms described herein or the like may be used, including but not limited to the valve system of FIG. 14. Valve system 200 may conveniently be coupled to a controller 310. In turn, controller 310 may be used to control the impedance level of valve system 200 in a manner similar to any of the embodiments described or incorporated herein. The level of impedance may be varied based on measurements of physiological parameters, or using a programmed schedule of changes. System 300 may include a wide variety of sensors and/or measuring devices to measure any of the physiological parameters described herein. These sensors or measuring devices may be integrated within or coupled to valve system 200 or facial mask, or may be separate.

For example, valve system 200 may include a pressure transducer for taking pressure measurements (such as intrathoracic pressures, intracranial pressures, intraocular pressures), a flow rate measuring device for measuring the flow rate of air into or out of the lungs, or a CO2 sensor for measuring expired CO2.

Examples of other sensors or measuring devices include a heart rate sensor 330, a blood pressure sensor 340, and a temperature sensor 350. These sensors may also be coupled to controller 310 so that measurements may be recorded. Further, it will be appreciated that other types of measuring devices may be used to measure various physiological parameters, such as oxygen saturation and/or blood levels of O2, blood lactate, blood pH, tissue lactate, tissue pH, blood pressure, pressures within the heart, intrathoracic pressures, positive end expiratory pressure, respiratory rate, intracranial pressures, intraocular pressures, respiratory flow, oxygen delivery, temperature, end tidal CO2, tissue CO2, cardiac output or the like.

In some cases, controller 310 may be used to control valve system 200, to control any sensors or measuring devices, to record measurements, and to perform any comparisons. Alternatively, a set of computers and/or controllers may be used in combination to perform such tasks. This equipment may have appropriate processors, display screens, input and output devices, entry devices, memory or databases, software, and the like needed to operate system 300.

A variety of devices may also be coupled to controller 310 to cause the person to artificially inspire. For example, such devices may comprise a ventilator 360, an iron lung cuirass device 370 or a phrenic nerve stimulator 380. Ventilator 360 may be configured to create a negative intrathoracic pressure within the person, or may be a high frequency ventilator capable of generating oscillations at about 200 to about 2000 per minute.

Example 1

The following is a non-limiting example illustrating how intracranial pressures may be lowered according to the invention. In this example, 30 kg pigs were anesthetized with propofol. Using a micromanometer-tipped electronic Millar catheter inserted below the dura, intracranial pressures were measured continuously in the spontaneously breathing pigs. Intrathoracic pressures (ITP) were recorded using a Millar catheter placed in the trachea at the level of the carina. After stabilizing the pigs blood pressure, heart rate, and ventilation rate, intracranial pressures (ICP) and intrathoracic pressures were recorded, with 0 cmH2O inspiratory impedance and then with inspiratory impedances of 5, 10, 15, and 20 cm H2O. Inspiratory impedance was achieved using an impedance threshold valve (ITV) as described in FIGS. 2-5.

Figure 7:
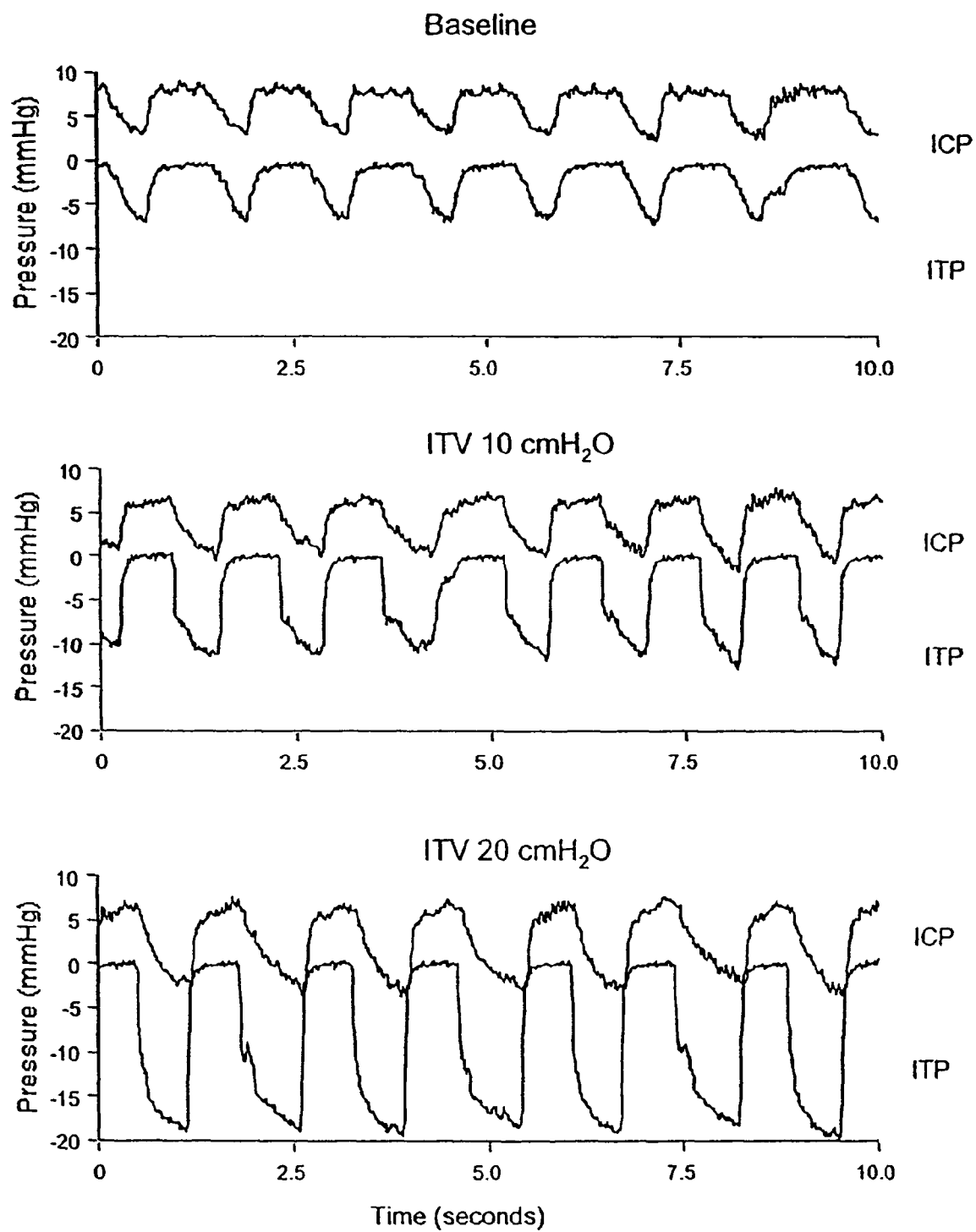
FIG. 7 is a series of graphs illustrating the lowering of intracranial pressures in an animal study.
Figure 8:
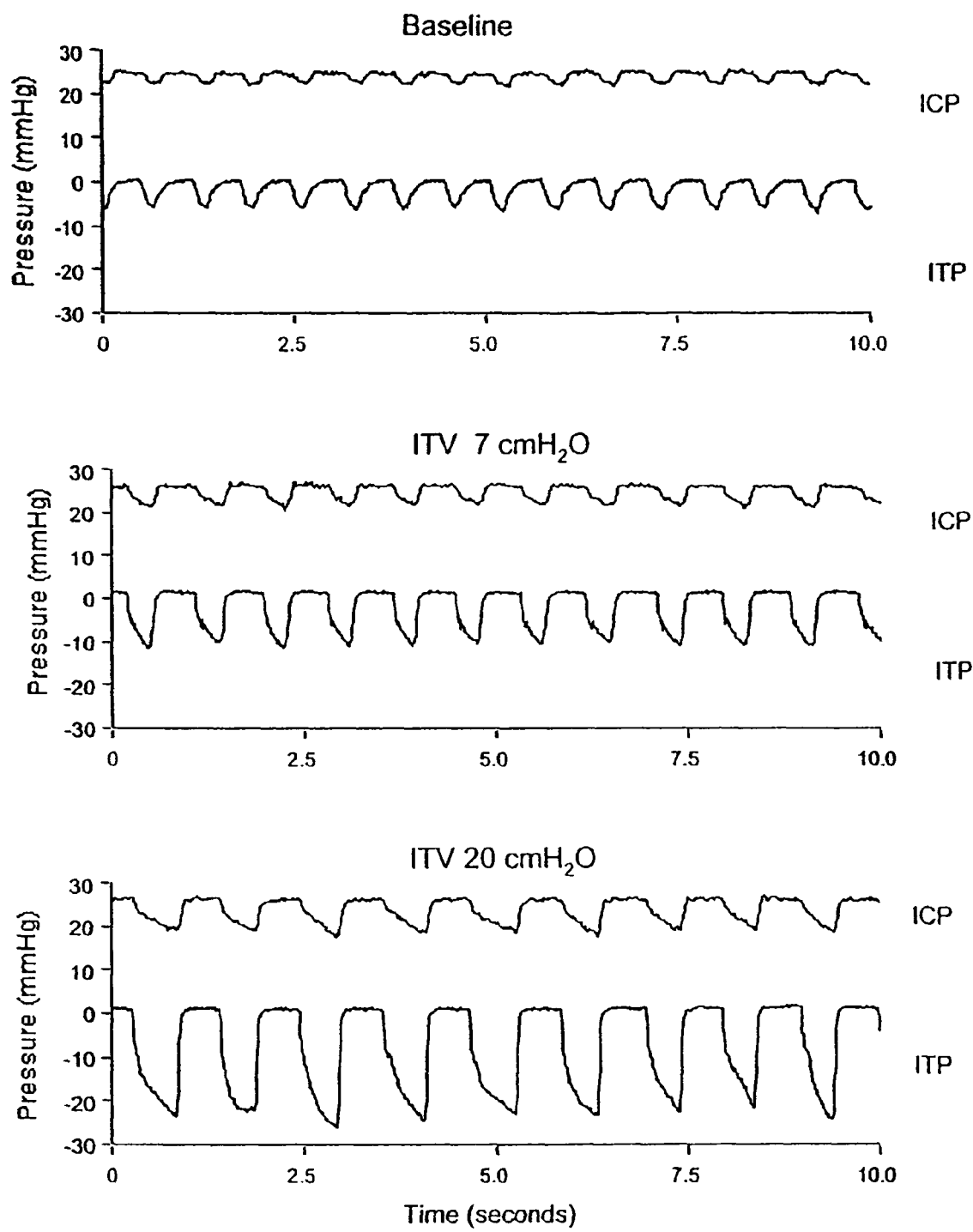
FIG. 8 is a series of graphs illustrating the lowering of intracranial pressures in another animal study.

At base, the intracranial pressure was approximately 8/4 mmHg. With increasing amounts of inspiratory impedance, the intracranial pressure was lowered proportionally as shown in FIG. 7. The intracranial pressure was 6/−2 mmHg when the pig breathed through an impedance of 20 cm H2O. These findings were observed in multiple pig studies and were reproducible. Next, the Millar catheter was inserted 3 cm into the pig's brain. The intracranial pressure increased secondary to the trauma associated with the insertion of the probe. The intracranial pressure increased to 25/22 mmHg at the new baseline. Next, the impedance threshold valve was evaluated at different levels of resistance (FIG. 8). Again, there was a decrease in intracranial pressure proportional to the degree of inspiratory impedance.

Example 2

In this example, intracranial pressures were increased in the setting of recovery from cardiac arrest. The example used a pig model with ventricular fibrillation for 6 minutes followed by cardiopulmonary resuscitation for 6 minutes, followed by defibrillation. Spontaneous breathing resulted in an up to 50% decrease in intracranial pressures when the animals breathed through an inspiratory impedance of 10 cm H2O using a valve system similar to Example 1.

In all examples above, the intrathoracic pressure decreased relative to the rest of the body, creating a suction effect that reduced the pressure in the venous blood vessels draining the brain, thereby reducing intracranial pressures.

The invention further provides techniques and devices for reducing intracranial pressure (ICP) by facilitating movement of cerebral spinal fluid (CFS). There are a number of causes of increased ICP including: head injury, ischemia, osmolar imbalance, cerebral edema, tumors, complications of dialysis, infections, stroke, hypertensive crises. Each can result in a slow, and in some cases, an acute rise in the ICP. The solid matter of the brain contents makes up about 80-85% of the material enclosed by the skull. Cerebral blood volume accounts for 3-6% and CSF for 5-15%. See, Anesthesia, Third Edition Editor, Ron Miller. Chapter authors: Shapiro and Drummond. Chapter 54 (1990), the complete disclosure of which is herein incorporated by reference. CSF moves within the brain from its site of production to its site of reabsorption in the brain in an unimpeded manner under normal physiological states. Since the contents in the brain are practically incompressible, a change in volume of any one of the three major components (brain matter, blood volume, CSF volume) results in a reciprocal change in one or both of the other brain components. When the volume of the brain expands, secondary to an increase in the non-CSF component(s), some of the CSF is forced to other locations, including through the foramen magnum (hole in skull connecting skull to space where the spinal cord is located) and into the CSF fluid space surrounding the spinal cord. When the non-CSF components expand in volume or size, the intracranial pressure rises. Normal ICP levels are 10-15 mmHg when supine. At levels greater than 15-20 mmHg, damage to the brain can occur secondary to compression and resultant tissue ischemia (lack of adequate blood flow). A reduction in ICP levels can be achieved by a number of clinical interventions including water restriction, diuretics, steroids, hyperventilation, a reduction of cerebral venous pressure, hypothermia, CSF drainage, and surgical decompression.

Increased ICP results in reduced CSF fluid movement and translocation. CSF fluid production generally remains constant (about 150 ml/day) despite elevated ICP. CSF fluid reabsorption is can be slowed by elevated ICP. By using the valve systems described herein, central venous pressures may be reduced. In turn, this results in a decrease in ICP and results in an increase in CSF fluid movement or translocation and reabsorption. This results in a further reduction in ICP.

The valve systems of the invention may be used in spontaneously breathing individuals, in patients ventilated with negative pressure ventilation or in patients ventilated with a ventilator that causes a decrease in central venous pressures for at least a portion of the respiratory cycle. Each time the intrathoracic pressure is reduced with the valve systems of the invention, there is a concomitant reduction in ICP and an increase in the movement of CSF. In other words, there is an increase in the difference between the peak and trough of the ICP wave form when using the valve systems. The sinusoidal movement occurs in spontaneously breathing people because of the change in pressure in the thorax that is transmitted to the brain via the venous blood vessels. The normally fluctuating CSF pressures (the pressure increases and decreases with each inspiration) are altered by the valve systems. More specifically, the valve systems create a lower trough value thereby creating an overall created change in the ICP with each inspiration. In the non-breathing patient, a similar effect can be produced with the valve systems when used with a variety of ventilator devices, including an iron lung, a phrenic nerve stimulator (such as those described in U.S. Pat. Nos. 6,234,985; 6,224,562; and 6,312,399, incorporated herein by reference), a suction cup on the chest that is used to periodically expand the chest and the like.

Figure 9A:
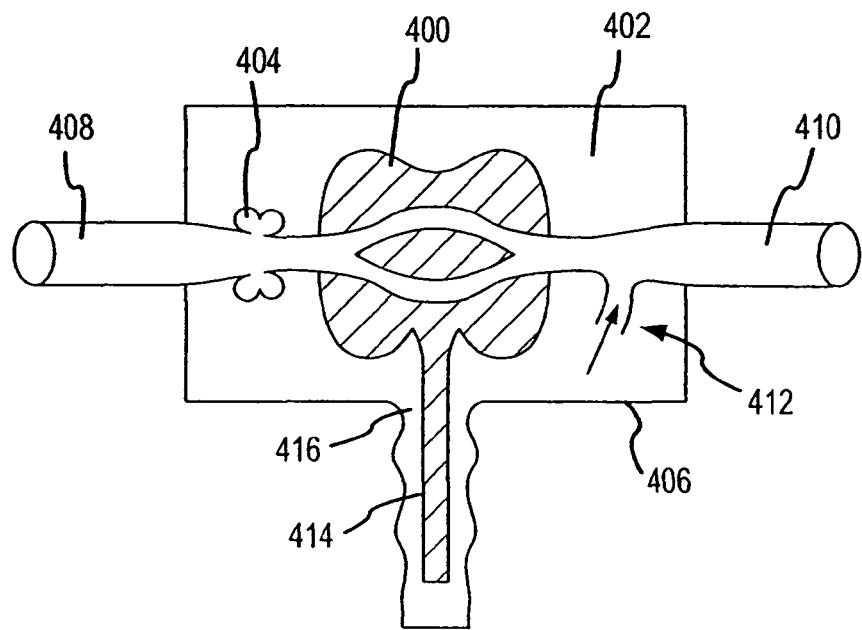
FIG. 9A is a schematic diagram of a person's brain under normal conditions.

Increased CSF fluid movement results in an overall improved metabolic state for the brain. This is shown schematically in FIGS. 9A and 9B. In FIG. 9A, the brain 400 is shown under normal conditions. The brain 400 is surrounded by CSF 402 which is produced at a site 404. The CFS in turn is surrounded by the skull 406. Blood enters brain 400 through an artery 408 and exits through a vein 410. Vein 410 also includes a site 412 of CFS drainage. Shown in FIG. 9A is an arrow showing the direction of CFS flow when draining. Extending from brain 400 is the spinal cord 414 that is surrounded by the foramen magnum 416.

Figure 9B:
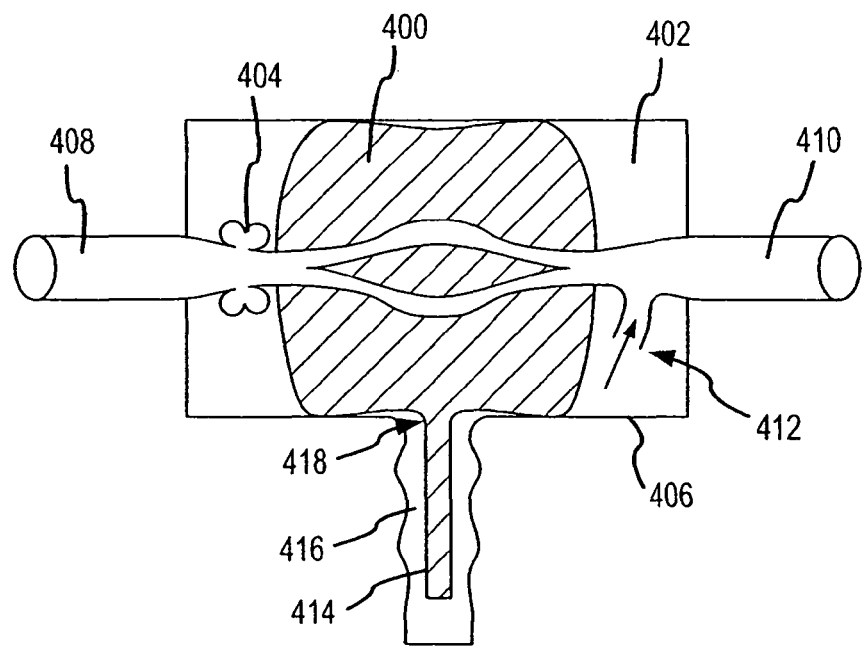
FIG. 9B illustrates the brain of FIG. 9A after increased swelling.

In FIG. 9B, the brain 400 is significantly swollen which reduces the space 402 where the CFS is located. The swelling of the brain 400 can cause blockage of CSF to the spinal cord 414 as shown by arrow 418. Also, movement of CSF to site 412 is reduced to hinder movement of CSF out of the skull 406.

By treating the elevated ICP associated with all of the conditions noted above using the valve systems described herein, brain swelling can be reduced. In so doing, CFS movement and fluid translocation is increased under those same conditions. This results in a further decrease in intracranial pressure as the CSF is able to relocate.

Figure 10:
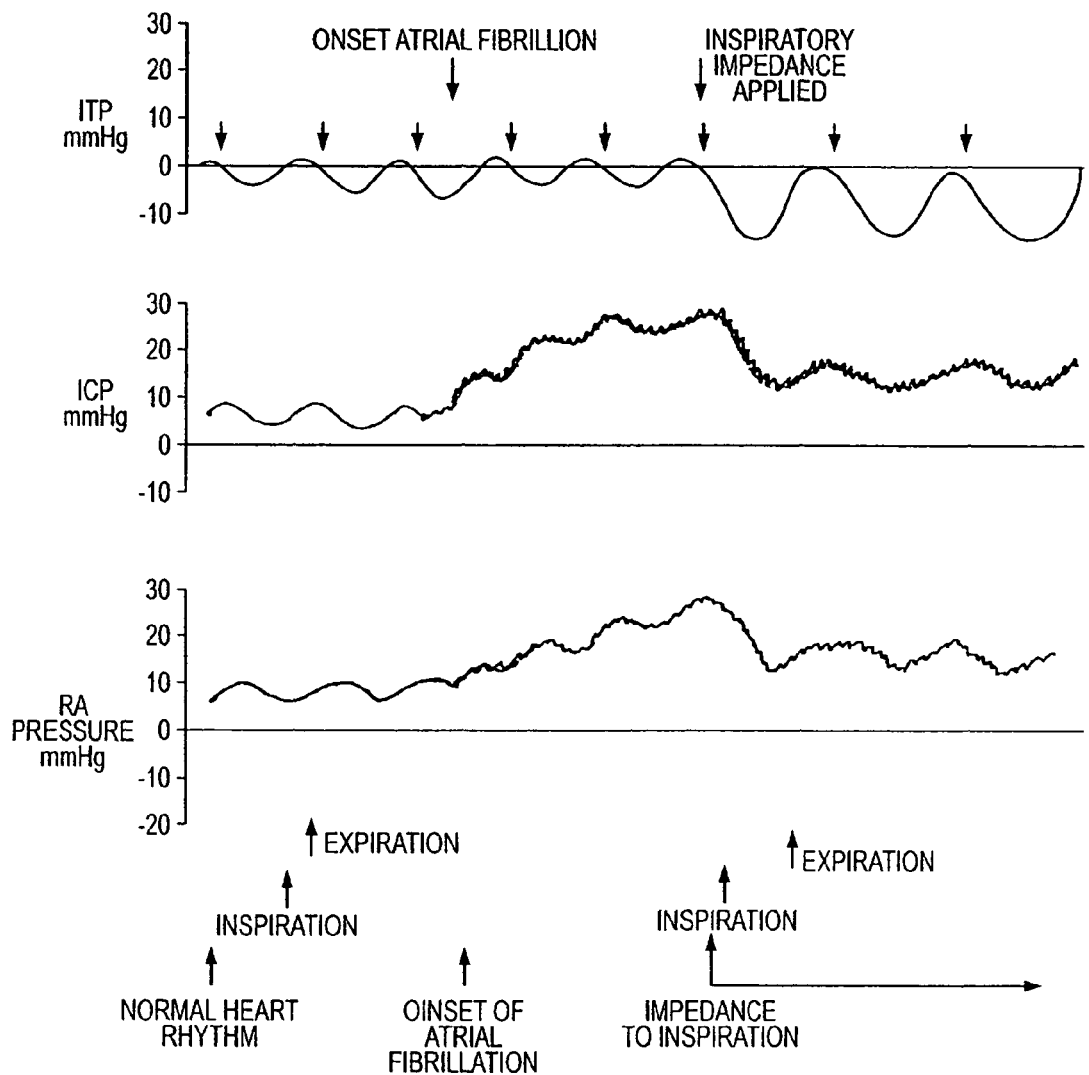
FIG. 10 shows three graphs illustrating the effect of lowering intrathoracic pressure on intracranial pressure and right atrial pressure.

Referring now to FIG. 10, the effects of contracting the atria of the heart on ICP will be described. As shown, contraction of the atria results in a phasic movement in ICP. This can be most clearly demonstrated during cardiac ventricular fibrillation. In that setting, the atria often beat spontaneously and the pressure of each contraction and relaxation waveform is transmitted immediately to the brain and is reflected in nearly identical fluctuations in ICP. The inventor has discovered that the fluid systems (venous blood vessels and CSF) are so closely linked, that subtle changes in the heart rhythm result in immediate changes in CSF pressure. Thus, in some patients with significant heart rhythms, or significant heart failure, the rise in right heart pressures as a result of these conditions results in an increase in ICP. Such rises in ICP can lead to a decrease in cerebral perfusion, since cerebral perfusion is determined by the pressure of the blood entering the brain (mean arterial pressure) minus the pressure of the blood leaving the brain (ICP and central venous pressure). Use of the valve and intrathoracic vacuum systems described herein will result in a decrease in intrathoracic pressure. As shown in FIG. 10, the downwardly pointing arrows represent the timing of each inhalation through the valve system. In the baseline state, before the onset of atrial fibrillation, each inspiration (small arrows) results in a reduction in ITP, a reduction of right atria pressure, a reduction in central venous pressures, and then an immediate reduction in ICP. With the onset of atrial fibrillation, the intracranial pressure rises and the sinusoidal pattern of ICP amplitude changes becomes dampened. As soon as the animal begins to inspire through an inspiration impedance of −10 cm H2O there is an immediate decrease in intrathoracic pressure (ITP), an immediate decrease in right atrial (RA) pressures, and an immediate decrease in intracranial pressure (ICP) along with the restoration of a sinusoidal fluctuation in ICP with each inspiration. With elevated ICP, inspiration through the impeding means results in a decrease in ICP, increased cerebral spinal fluid flow, and a decrease in cerebral ischemia secondary to increased cerebral perfusion. As such, the valve systems can used in patients with heart rhythms, such as atrial fibrillation, or patients with heart failure who have increased ICP in order to reduce their ICP, increase CSF fluid movement and translocation, and ultimately help them to improve their brain function.

Hence, the amount of inspiratory resistance, or the amount of negative intrathoracic pressure generation (which may be generated using a variety of techniques) can be controlled or regulated by feedback from measurement of ICP, blood pressure, respiratory rate, or other physiological parameters. Such a system could include a closed loop feedback system.

Figure 11:
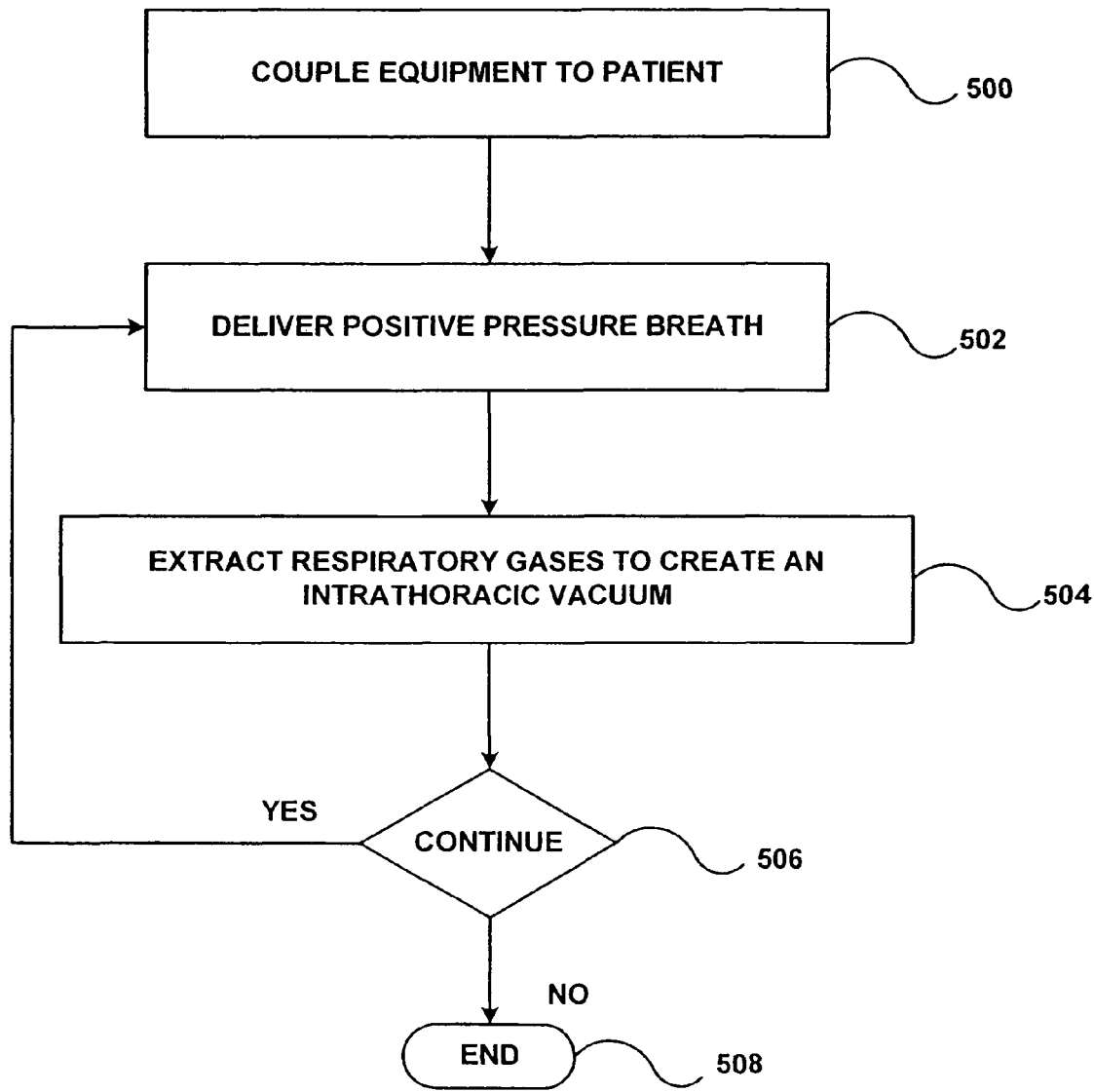
FIG. 11 is a flow chart illustrating another method for reducing intracranial and intraocular pressures according to the invention.

FIG. 11 is a flow chart illustrating another method for treating a person suffering from head trauma associated with elevated intracranial pressures. In so doing, it will be appreciated that such techniques may also be used to treat those suffering from low blood pressure or those in cardiac arrest, among others. The techniques are particularly useful in cases where the person is not breathing, although in some cases they could be used for breathing patients as well.

In a broad sense, when treating a person suffering from head trauma, a person's intrathoracic pressure is lowered to decrease intracranial pressures. In turn, this assists in reducing secondary brain injury. As shown in step 500, equipment may be coupled to the person to assist in lowering the person's intrathoracic pressure. A wide variety of equipment and techniques may be used to decrease the intrathoracic pressure, including using a mechanical ventilator capable of extracting respiratory gases, such as the one described in U.S. Pat. No. 6,584,973, a phrenic nerve or other muscle stimulator (with or without the use of an impedance mechanism, such as those described in U.S. Pat. Nos. 5,551,420; 5,692,498; 6,062,219; 5,730,122; 6,155,257; 6,234,916 and 6,224,562) such as those described in U.S. Pat. Nos. 6,234,985; 6,224,562; 6,312,399; and 6,463,327, an iron lung device, a thoracic vest capable of pulling outward on the chest wall to create an intrathoracic vacuum similar to the effect of an iron lung, a ventilatory bag, such as the one described in copending U.S. application Ser. No. 10/660,366, filed Sep. 11, 2003, filed on the same date as the present application, and the like. The complete disclosures of all these references are herein incorporated by reference. For breathing patients, a threshold valve as described above and that is set to open when about 5 cmH2O is generated during an inhalation may be used to enhance the person's negative intrathoracic pressure.

When the person is not breathing, a positive pressure breath is delivered to the person as illustrated in step 502. This may be done with a mechanical ventilator, a ventilatory bag, mouth to mouth, and the like. This is followed by an immediate decrease in intrathoracic pressure. This may be done by extracting or expelling respiratory gases from the patient's lungs as shown in step 504. Any of the techniques described above may be used to lower the intrathoracic pressure. Such a reduction in intrathoracic pressure also lowers central venous pressure and intracranial pressure.

The vacuum effect during the expiratory phase may be constant, varied over time or pulsed. Examples of different ways to apply the vacuum are described later with respect to FIGS. 12A-12C. The initial positive pressure breath may be supplied for a time of about 250 milliseconds to about 2 seconds, and more preferably from about 0.75 seconds to about 1.5 seconds. The respiratory gases may be extracted for a time that is about 0.5 to about 0.1 to that of the positive pressure breath. The positive pressure breath may be delivered at a flow rate in the range from about 0.1 liters per second to about 5 liters per second, and more preferably from about 0.2 liters per second to about 2 liters per second. The expiratory flow (such as when using a mechanical ventilator) may be in the range from about 0.1 liters per second to about 5 liters per second, and more preferably from about 0.2 liters per second to about 2 liters per second. The vacuum may be maintained with a negative flow or without any flow. The vacuum may be in the range from about 0 mmHg to about −50 mmHg, and more preferably from about 0 mmHg to about −20 mmHg.

As shown in step 506, the process of delivering a positive pressure breath and then immediately lowering intrathoracic pressures may be repeated as long as necessary to control intracranial pressures. Once finished, the process ends at step 508.

Figure 12A:
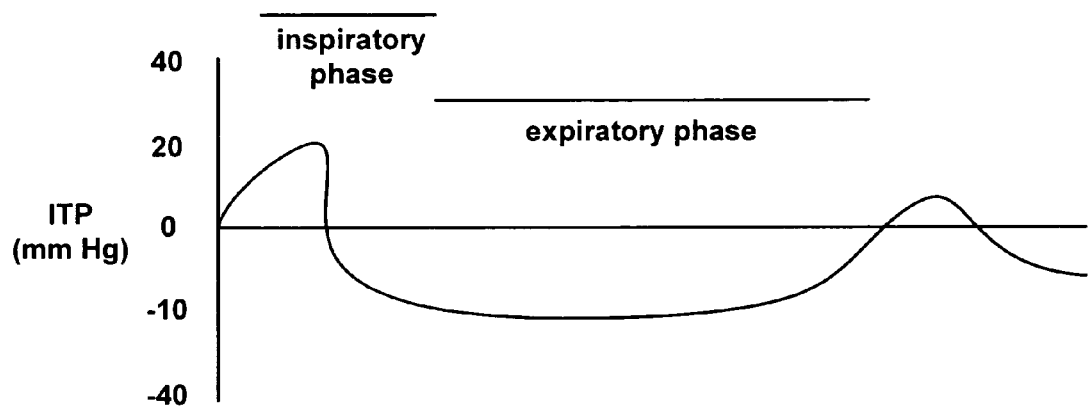
FIGS. 12A-12C show three graphs illustrating patterns for delivering a positive pressure breath and extracting respiratory gases according to the invention.
Figure 12B:
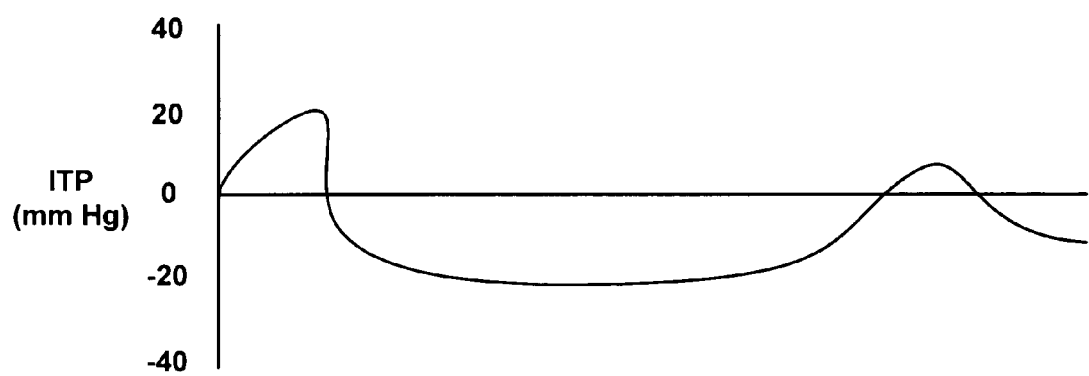
Figure 12C:
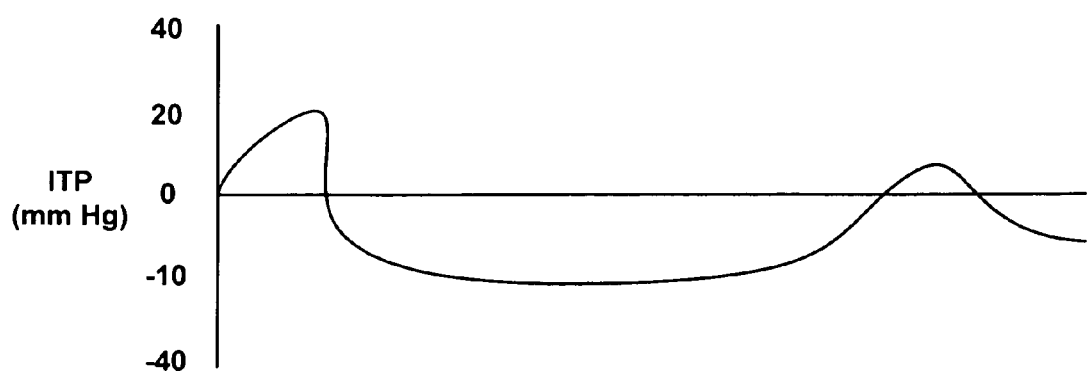

The manner in which positive pressure breaths and the vacuum are created may vary depending upon a particular application. These may be applied in a variety of waveforms having different durations and slopes. Examples include using a square wave, biphasic (where a vacuum is created followed by positive pressure, decay (where a vacuum is created and then permitted to decay), and the like. Three specific examples of how this may occur are illustrated in FIGS. 12A-12C, although others are possible. For convenience of discussion, the time during which the positive pressure breath occurs may be defined in terms of the inspiratory phase, and the time during which the intrathoracic pressure is lowered may be defined in terms of the expiratory phase. The positive pressure breaths may occur at about 10 to about 16 breaths per minute, with the inspiratory phase lasing about 1.0 to about 1.5 seconds, and the expiration phase lasing about 3 to about 5 seconds. As shown in FIG. 12A, respiratory gases are quickly supplied up to a pressure of about 22 mmHg. This is immediately reversed to a negative pressure of about −10 mmHg. This pressure is kept relatively constant until the end of the expiratory phase where the cycle is repeated.

In FIG. 12B, the positive pressure is more slowly applied. When reaching a pressure of about 10 to about 15 mmHg, the pressure is rapidly reversed to a negative pressure of about −20 mmHg. The negative pressure gradually declines to about 0 mmHg at the end of the expiratory phase. The cycle is then repeated. Hence, in the cycle of FIG. 12B, the positive pressure is reduced compared to the cycle in FIG. 12A, and the negative pressure is initially lower, but allowed to gradually increase. The technique is designed to help reduce a possible airway collapse.

In FIG. 12C, the positive pressure is brought up to about 20 mmHg and then immediately brought down to about 0 mmHg. The negative pressure is then gradually increased to about −20 mmHg toward the end of the expiratory phase. This cycle is designed to help reduce a possible airway collapse.

Figures 13A, 13B:
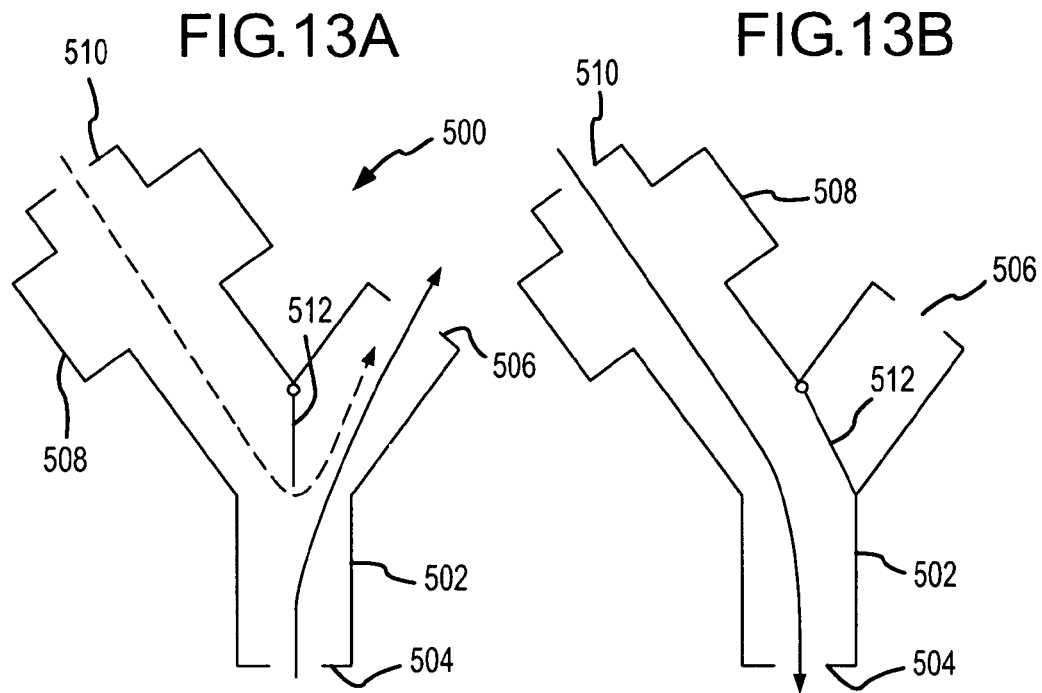
FIGS. 13A and 13B schematically illustrate one device that may be used to lower intrathoracic pressures with a non-breathing patient according to the invention.

FIGS. 13A and 13B schematically illustrate one embodiment of a device 500 that may be used to lower intrathoracic pressures in a non-breathing patient. Device 500 comprises a housing 502 having an interface opening 504 that may be directly or indirectly coupled to the patient's airway using any type of patient interface. Housing 502 also includes a vacuum source interface 506 that may be in fluid communication with any type of device or system capable of producing a vacuum. Also coupled to housing 502 is a means to regulate the vacuum, such as a pressure responsive valve system 508. Device 500 further includes a ventilation interface 510 that may be used to provide a breath to the patient, if needed, when the vacuum is not applied.

In this embodiment, the vacuum may be provided by essentially any type of a vacuum source, and the regulator may comprise an impedance valve, such as those described in U.S. Pat. Nos. 5,551,420; 5,692,498; 6,062,219; 5,730,122; 6,155,257; 6,234,916; 6,224,562; 6,234,985; 6,224,562; 6,312,399; and 6,463,327 as well as others described herein. To supply a breath, a variety of ventilation sources may be used, such as, for example, a bag valve resuscitator, that is coupled to interface 510. Device 500 may further include a mechanism 512 to inhibit the vacuum when delivering a breath to the patient from the bag valve resuscitator. Once the breath is delivered, mechanism 512 operates to permit the vacuum within the thorax to be reapplied. The mechanism 512 used to turn off and on the vacuum source can include a slider switch that moves to close off the branch in housing 500 having the vacuum source as illustrated in FIG. 13B. However, other types of switches or mechanisms may be used. In some cases, the vacuum source may have a controller that is configured to shut off the vacuum when the breath is administered so that mechanism 512 is not needed. Also, a controller and appropriate sensors could be used to sense when the breath is delivered and stopped so that mechanism 512 may be appropriately operated by the controller. After the breath is delivered, mechanism 512 moves back to the position illustrated in FIG. 13A so that the vacuum may be supplied to the patient. When the vacuum reaches a threshold amount, regulator 508 operates to maintain the level of vacuum at about the threshold amount.

Figures 14A, 14B:
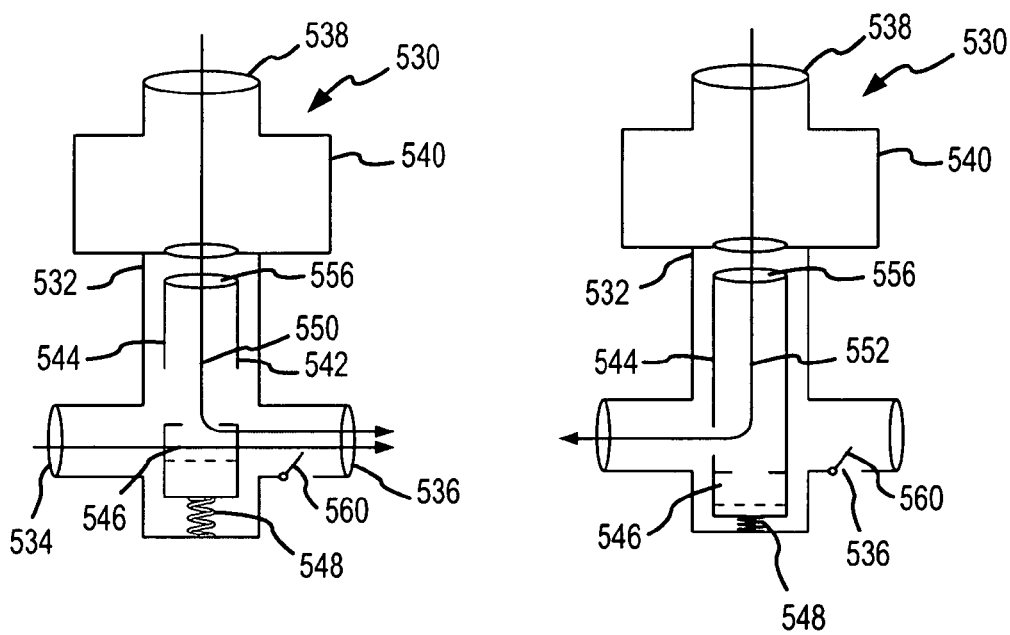
FIGS. 14A and 14B illustrate another device that may be used to lower intrathoracic pressures with a non-breathing patient according to the invention.

FIGS. 14A and 14B illustrate another embodiment of a device 530 that may be used to treat a patient. Device 530 operates using similar principles as device 500 illustrated in FIGS. 13A and 13B. Device 530 comprises a housing 532 having a patient interface 534 that may be coupled to the patient's airway and a vacuum interface 536 that may be coupled to a vacuum source. Housing 532 also includes a ventilation interface 538 through which a positive pressure breath may be supplied. Also coupled to housing 532 is a vacuum regulator 540 that regulates the amount of vacuum supplied to the patient. One example of a flow regulator that may be used is described below with references to FIGS. 15A and 15B. However, it will be appreciated that any of the flow regulators described herein may be used. Disposed within housing 532 is a flow control device 542 that is used orchestrate gas flows through housing 532. Flow control device 542 comprises a cylindrical member 544 that may slide within housing 532 and includes a flow path 546 that permits gas flow between interfaces 534 and 536 when flow control device 542 is in the position illustrated in FIG. 14A. Conveniently, a spring 548 or other biasing mechanism is used to hold flow control device 542 in the home position illustrated in FIG. 14A. Flow control device 542 also includes a flow path 550 illustrated by the arrow in FIG. 14A to permit gas flows between regulator 540 and interface 536. Hence, when in the home position, a vacuum may be supplied through interface 536 which lowers the person's intrathoracic pressure. If the vacuum becomes to great, gas flows are permitted through regulator 540 to lower the amount of vacuum.

As illustrated in FIG. 14B, flow control device 542 also includes a flow path 552 that passes from interface 538 to interface 534. This permits a positive pressure breath to be supplied to the patient through interface 538. More specifically, as gasses are injected through interface 538, they flow into flow control device 542 causing it to move within housing 532 and compress spring 548. In so doing, flow path 546 closes as it becomes blocked by housing 532. Flow path 550 also closes, leaving only flow path 552 opened to permit the respiratory gases to flow to the patient. When the positive pressure breath stops, spring 548 forces flow control device back to the home position where the vacuum is once again supplied to the patient.

Hence, when a vacuum is applied from interface 536, air is pulled out of the patient through interface 534 until the cracking pressure of the impedance valve 540 is reached. At that point air passes through impedance valve 540 from the ventilation source at interface 538, thereby setting the limit of the vacuum achieved in the patient. When positive pressure ventilation is delivered from the ventilation source at interface 538, the internal slider switch cylinder 542 moves downward to close off the vacuum source, allowing for delivery of a positive pressure volume to provide a breath to the patient. Flow control device 542 may include a cup-shaped opening 556 which helps to move the device 542 along with minimal force applied. Once the breath has been delivered, and there is no positive force delivered from the ventilation source to the device 542, spring 548 pushes upwards, re-exposing the patient to the vacuum source.

Device 530 may also include an optional pressure pop-off regulator 560. In the event that the vacuum source is too great, the pop-off regulator 560 opens allowing for pressure relief above the desired vacuum pressure. The pop-off regulator 560 may be configured to open for pressures greater than about 20 to about 100 mmHg.

Although the devices illustrated in FIGS. 13 and 14 are shown with mechanical switching mechanisms (to turn the vacuum off and on), others may also be used, such as magnetic, electronic, or electrical. Other kinds of possible switches include a ball valve, flapper valve, fish mouth valve, or other mechanical means as well as electric or electronic valving systems, including a solenoid, to allow for temporary inhibition of the vacuum once the positive pressure breath is delivered from the ventilation source. Additional regulators can also be used on the vacuum source to limit the flow or force of the vacuum. For example, the vacuum source could be configured to provide a constant vacuum once a threshold level has been achieved. In addition, the vacuum regulator and impedance valves 508 and 530 may be variable or set at a fixed level of impedance. The vacuum source may also be a suction line or come from a venture device attached to an oxygen tank that could both provide oxygen to the patient and a vacuum source. Further, the invention is not limited to using an impedance valve, as shown, to regulate the vacuum. Multiple switching and regulating means may be used instead. The ventilation source is similarly not limiting and may include sources such as mouth-to-mouth, a bag-valve resuscitator, an automatic ventilator, and the like.

Figure 15A:
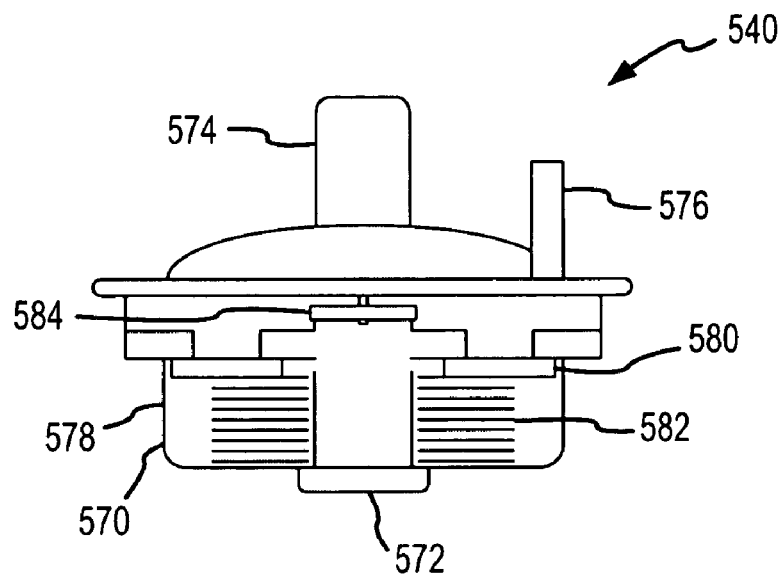
FIGS. 15A and 15B illustrate one embodiment of a threshold valve system that may be used with the device of FIGS. 14A and 14B.
Figure 15B:
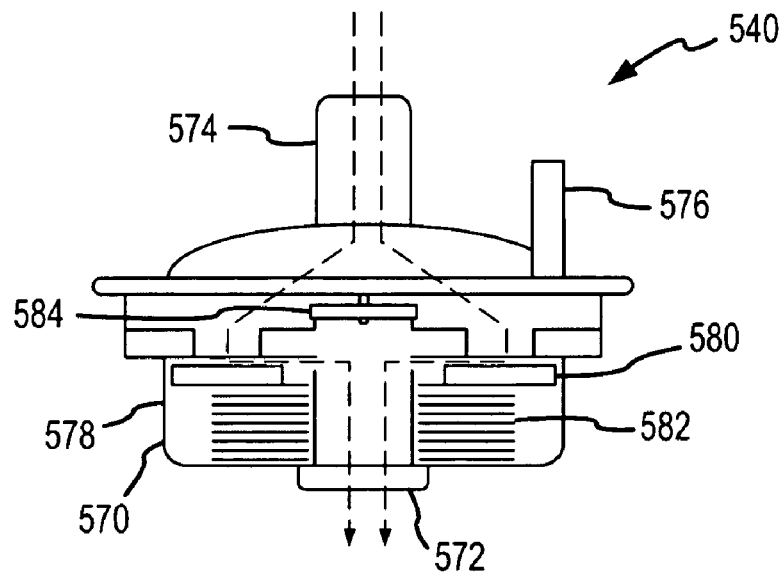

FIGS. 15A and 15B illustrate flow regulator 540 in greater detail. Regulator 540 comprises a housing 570 having a patient port 572 and a ventilation port 574. Optionally, a supplemental oxygen port 576 may also be provided. Gas may flow through housing 570 (between ports 572 and 574) through one of two flow paths. The first flow path is blocked by a one way check valve 578 that comprises a check valve gasket 580 and a spring 582. The second flow path is blocked by a diaphragm 584.

In operation, a vacuum is experienced at patient port 572 as the vacuum source draws a vacuum at port 536 (See FIG. 14A). When the vacuum reaches a threshold level, spring 582 compresses to move gasket 580 downward, thereby creating a flow path as illustrated in FIG. 15B. As the vacuum is pulled, diaphragm 584 closes to prevent air from flowing through the other flow path. Gasket 580 remains spaced apart from the opening as long as the vacuum is at the threshold level. In this way, regulator 540 is able to maintain the vacuum at a constant level.

When ready to ventilate the patient, the vacuum is stopped and respiratory gases are injected into port 574 and/or port 576. These gasses lift diaphragm 584 to permit the gases to flow to the patient.

Example 3

Example 3 is another non-limiting example illustrating how intracranial pressures and intrathoracic pressures may be lowered and systolic arterial pressure may be increased according to one aspect of the invention. In this example, 30 kg pigs were anesthetized with propofol. Using a micromanometer-tipped electronic Millar catheter inserted 2 cm below the dura, intracranial pressures were measured in non-breathing pigs. Intrathoracic pressures (ITP) were recorded using a Millar catheter placed in the trachea at the level of the carina. Systolic aortic blood pressures (SBP) were measured in the aorta with a Millar catheter. To regulate intrathoracic pressures, a system similar to that illustrated in FIGS. 14A, 14B, 15A and 15B was used, with inspiratory impedance (−8 cm H2O with a flow rate of 30 L/min). Positive pressure ventilation was provided at a rate of 10 breaths/min with a tidal volume of approximately 400 ml delivered over 1.0 seconds with an automatic transport ventilator. The objectives, methods, results, and conclusions describing these novel cardiopulmonary-cranial interactions are summarized below.

An objective of this example was to evaluate the acute use of a novel inspiratory impedance threshold device (ITD) attached to a controlled but continuous vacuum (CV) source to decrease intrathoracic pressure (ITP) and intracranial pressure (ICP) but simultaneously increase mean arterial pressure (MAP), coronary perfusion pressure (CPP) and cerebral perfusion pressure (CerPP) in an apneic pig model of sequential insults of cardiac arrest and fixed-bleed hemorrhage hypotensive shock. This animal model is associated with both elevated ICP after cardiac arrest and significant hypotension after hemorrhage.

This example used 6 female farm pigs (28-32 kg) that were anesthetized with propofol, intubated and ventilated to maintain normocarbia and O2 saturation >90%. Ventricular fibrillation was induced and followed by 6 min of no treatment, 6 min of standard CPR, and then defibrillation. After return of spontaneous circulation and while ventilated mechanically at 10 breaths/min, 35% of blood volume was removed with a rate of 60 cc/min. Five min later ITD-CV was applied for 5 min along with positive pressure ventilation with 100% oxygen at a rate of 10 bpm. The ITD-CV was then removed and positive pressure ventilation at a rate of 10 breaths/min was reapplied. Hemodynamic parameters and arterial blood gases were assessed before, during, and after ITD-CV application. Statistical analysis was performed with a paired t-test and ANOVA to compare +/−ITD-CV use.

The results are summarized in the Table below. As shown, by regulating thoracic pressures, use of the ITD-CV causes an instantaneous decrease in ITP and ICP as well as a rapid rise in MAP and a marked increase in CerPP. Hence, the ITD-CV may be used to treat hypotension, shock, and cerebral hypertension.

TABLE

|  | Before ITD-CV | During ITD-CV | After ITD-CV | p value |
| --- | --- | --- | --- | --- |
| ITP | 0.5 ± 0.1 | −12.0 ± 1.1 | 0.1 ± 0.2 | 0.001 |
| MAP | 46.7 ± 5.2 | 54.7 ± 7.7 | 38.3 ± 4.1 | 0.03 |
| ICP | 14.1 ± 3.9 | 6.1 ± 4.5 | 15.4 ± 3.9 | 0.001 |
| CerPP | 32.7 ± 4.2 | 48.6 ± 5.9 | 23.0 ± 4.5 | 0.01 |
| CPP | 40.1 ± 4.5 | 58.4 ± 7.7 | 31.1 ± 3.4 | 0.008 |

In one particular embodiment, a person may have his or her intrathoracic pressure manipulated using multiple techniques, alone or in combination. For example, some type of external thoracic positive pressure source may be used to increase and then decrease the person's intrathoracic pressure to move blood out of and then into the heart and lungs in a repetitive fashion. Examples of such an external thoracic positive pressure source include a mechanical extrathoracic vest, a body cuirass, a compression piston, a compression cup, or the like. Such devices may function as non-invasive hemodynamic support devices for maintenance of increase blood pressure and circulation in hypotensive patients.

While the person's intrathoracic pressures are being externally manipulated (e.g., being increased and decreased), the person may also have his or her intrathoracic pressures manipulated by applying positive pressure breaths and a vacuum using any of the techniques described herein. Further, any of the valve systems described herein may be used in combination as well. Hence, while the person's chest is being compressed and relaxed, positive pressure breaths followed by a vacuum may be applied at the same time. In this way, non-invasive techniques are provided for improving blood flow to the vital organs for an indefinite period of time, and may be used in cases where the patient is in shock, has very low blood pressure, those in cardiac arrest, and the like. Also, such techniques may be used to circulate a preservative solution, equivalent to cardioplegic agents, until more definitive care is available.

The timing of each of these steps may be controlled to correlate in any manner, such as, for example, applying the vacuum while the force on the patient's chest is relaxed. Also, the timing of chest compressions could be tied to other variables, such as timing the compressions and/or decompressions with intrinsic cardiac rhythm (i.e., ECG activity). Further, the positive pressure breaths may be performed only as needed and not in association with every chest compression. Further, the chest may be decompressed only after a certain number of chest compressions.

As with other embodiments, the patient may also be supplied with periodic positive pressure ventilation or an extracorporeal oxygenator to provide adequate respiration. Negative pressure ventilation may also be used to provide proper ventilation. For example, the chest may be decompressed with an unimpeded airway to provide the negative pressure ventilation. Also, the techniques just described could also be used alone or in combination with invasive ways to also maintain blood pressure. For instance, a greater effect on intracranial pressure may be produced if some of the patient's blood is removed from the body.

One particular arrangement of a system that may be used with such techniques is set forth in FIG. 6 (previously described) where element 370 (an iron lung cuirass device) may also schematically represent any of the external thoracic positive pressure sources described herein. Further, controller 310 may also include some type of energy source for operating the positive pressure source, such as pneumatic, electronic, combustion or the like. In this way, a variety of energy sources may be used to compress the chest and then release the compression in an alternating manner. Ventilator 360 may be used to apply the positive pressure breath followed by a vacuum using any of the techniques described herein, as well as to provide proper ventilation. Further, although shown with valve system 200, it will be appreciated that any of the other valve systems described herein may be used as well. Also, it will be appreciated that temperature sensor 350 may be substituted with other types of sensors and/or monitors, such as an ECG monitor, so that chest compressions and/or decompressions may be timed with ECG activity.

The invention has now been described in detail for purposes of clarity and understanding. However, it will be appreciated that certain changes and modifications may be practiced within the scope of the appended claims.

What is claimed is:

1. A medical method for treating a person, the method comprising:
   repetitively compressing the person's chest to provide a compression phase where the chest is compressed and a relaxation phase where the chest is permitted to expand;
   while repeatedly compressing the person's chest, extracting respiratory gases from the person's airway using a vacuum to create an intrathoracic vacuum to lower pressures in the thorax, and wherein the intrathoracic vacuum is sustained continuously over multiple, successive chest compression and relaxation phases.

2. A method as in claim 1, wherein the pressures are lowered in the thorax in order to enhance blood flow back to the heart.

3. A method as in claim 1, wherein the pressures are lowered in the thorax in order to lower intracranial pressures.

4. A method as in claim 1, wherein the pressures are lowered in the thorax in order to enhance cerebral perfusion pressures.

5. A method as in claim 1, further comprising at least periodically delivering a positive pressure breath to the person to provide ventilation.

6. A method as in claim 5, further comprising stopping application of the vacuum when applying the positive pressure breath using a vacuum regulator.

7. A method as in claim 5, further comprising stopping application of the vacuum when applying the positive pressure breath using a vacuum switching arrangement.

8. A method as in claim 5, wherein the positive pressure breath is delivered using source selected from a group consisting of a mechanical ventilator, a hand held bag valve resuscitator, mouth-to-mouth, or a means to provide intermittent positive pressure ventilation.

9. A method as in claim 5, wherein the time the positive pressure breath is supplied relative to the time in which respiratory gases are extracted is in the range from about 0.5 to about 0.05.

10. A method as in claim 5, wherein the respiratory gases are lowered to an intrathoracic pressure of about −5 mmHg to about −10 mmHg and then kept generally constant until the next positive pressure breath.

11. A method as in claim 5, wherein the positive breath is delivered and the respiratory gases are rapidly lowered to an intrathoracic pressure of about −5 mmHg to about −20 mmHg and then gradually reduced towards about 0 mmHg.

12. A method as in claim 1, wherein the person is suffering from ailments selected from a group consisting of elevated intracranial pressures, shock, low blood pressure, low blood circulation, low blood volume, cardiac arrest and heart failure.

13. A method as in claim 1, further comprising regulating the amount of intrathoracic vacuum using a threshold valve that is in fluid communication with the person's airway, wherein the threshold valve is configured to open when the person's negative intrathoracic pressure reaches about −3 cm H2O to about −20 cm H2O to permit respiratory gases to flow into the person's airway.

14. A method as in claim 1, wherein the step of repetitively compressing the person's chest comprises coupling an external thoracic positive pressure source to the chest, wherein the thoracic positive pressure source is selected from a group consisting of a mechanical extrathoracic vest, a body cuirass, a compression piston, and a compression cup.

15. A method as in claim 1, wherein the respiratory gases are extracted with a constant extraction, varied over time, or a pulsed extraction.

16. A method as in claim 1, wherein the breath is delivered for a time in the range for about 250 milliseconds to about 2 seconds, wherein the breath is delivered at a rate in the range from about 0.1 liters per seconds to about 5 liters per second, and wherein the vacuum is maintained at a pressure in the level from about 0 mmHg to about −25 mmHg.

17. A method as in claim 1, further comprising timing the chest compressions with cardiac rhythm.

18. A method as in claim 1, wherein negative intrathoracic pressure is generated using equipment selected from a group consisting of a mechanical ventilator, a vacuum with vacuum regulator, a phrenic nerve stimulator, an extrathoracic vest, a ventilator bag, a chest tube attached to a vacuum source, an active chest compression/decompression device, and an iron lung cuirass device.

19. A method as in claim 1, wherein the intrathoracic pressures are lowered to a pressure of about −3 mmHg to about −20 mm Hg.

20. A device for lowering a patient's intrathoracic pressures, the device comprising:
   a means external to the patient for repeatedly increasing and decreasing intrathoracic pressures during a chest compression phase and relaxation phase;

a means to interface with the patient's airway;

a means to extract respiratory gases from the patient's thorax to create and at least periodically maintain a negative intrathoracic pressure; and a means to repeatedly regulate the extraction of respiratory gases from within the patient's lungs and airway such that the negative intrathoracic pressure is maintained continuously over multiple, successive chest compression and relaxation phases.

21. A device as in claim 20, further comprising a means to deliver a positive pressure breath, to periodically provide inspiration of respiratory gases.

22. A device as in claim 21, further comprising a switching mechanism to stop the extraction of respiratory gases during delivery of a positive pressure breath, wherein the switching mechanism is selected from a group consisting or mechanical devices, magnetic devices, and electronic devices.

23. A device as in claim 21, wherein the means for delivering a positive pressure breath is selected from a group consisting of a mechanical ventilator, a hand held bag valve resuscitator, mouth-to-mouth, or a means to provide intermittent positive pressure ventilation.

24. A device as in claim 20, wherein the means external to the patient for repeatedly increasing and decreasing intrathoracic pressures is selected from a group consisting of a mechanical extrathoracic vest, a body cuirass, a compression piston, and a compression cup.

25. A device as in claim 20, wherein the means to extract respiratory gases comprises vacuum source selected from a group consisting of a suction line, a push-pull resuscitator bag, or venturi device attached to an oxygen tank.

26. A device as in claim 20, wherein the means for decreasing intrathoracic pressures further comprises a vacuum source connected to a chest tube.

27. A device as in claim 20, wherein the means for extracting respiratory gases is selected from a group consisting of a mechanical ventilator, a vacuum with vacuum regulator, a phrenic nerve stimulator, an extrathoracic vest, an active chest compression decompression device, a ventilator bag, and an iron lung cuirass device.

28. A device as in claim 20, wherein the means for regulating comprises a threshold valve that is in fluid communication with the person's airway.

29. A device as in claim 28, wherein the threshold valve is configured to open when the person's negative intrathoracic pressure reaches about −3 cm H2O to about −20 cm H2O to permit respiratory gases to flow into the person's airway.

30. A device for lowering a person's intrathoracic pressures, the device comprising:

an external thoracic positive pressure source for repetitively compressing the person's chest to produce a chest compression phase and relaxation phase;

a housing having an interface that is adapted to couple the housing to the person's airway;

a vacuum source in fluid communication with the housing for extracting respiratory gases from the person's lungs and airway to create and at least periodically maintain a negative intrathoracic pressure;

a vacuum regulator to regulate the extraction of respiratory gases from the patient's lungs and airway such that the negative intrathoracic pressure is maintained continuously over multiple, successive chest compression and relaxation phases.

31. A device as in claim 30, further comprising a positive pressure source in fluid communication with the housing for intermittently supplying positive pressure breaths to the person.

32. A device for increasing and decreasing a person's intrathoracic pressures, the device comprising:

an external thoracic positive pressure source for repetitively compressing the person's chest to produce a chest compression phase and relaxation phase;

a housing having an interface that is adapted to couple the housing to the person's airway;

a vacuum source in fluid communication with the housing for extracting respiratory gases from the person's lungs and airway to create and at least periodically maintain a negative intrathoracic pressure;

a vacuum regulator to regulate the extraction of respiratory gases from the patient's lungs and airway such that the negative intrathoracic pressure is maintained continuously over multiple, successive chest compression and relaxation phases;

a timer that is configured to provide information to the vacuum regulator to periodically inhibit the extraction of respiratory gases to allow for inspiration of respiratory gases when decreasing a person's intrathoracic pressures.

33. A device as in claim 32, further comprising periodically delivering a positive pressure breath by a ventilation source.

34. A medical method for treating a person, the method comprising:

repetitively compressing and actively decompressing the person's chest;

at least periodically, extracting respiratory gases from the person's airway using a vacuum to create an intrathoracic vacuum to lower pressures in the thorax, and wherein the intrathoracic vacuum is sustained continuously over multiple, successive chest compressions and decompressions;

allowing respiratory gases to flow generally unimpeded to the lungs during at least some of the chest compressions and decompressions to provide oxygenated gases to the person's lungs.

35. A method as in claim 34, further comprising at least periodically providing a positive pressure breath to the person to provide ventilation.

36. A method as in claim 34, where the person's chest is actively decompressed after only certain number of chest compressions.

37. A method as in claim 34, further comprising reducing the patient's blood volume.

38. A method as in claim 34, further comprising timing the chest compressions with cardiac rhythm.

* * * * *

UNITED STATES PATENT AND TRADEMARK OFFICE
CERTIFICATE OF CORRECTION

PATENT NO. : 7,766,011 B2  Page 1 of 1
APPLICATION NO. : 11/034996
DATED : August 3, 2010
INVENTOR(S) : Keith G. Lurie It is certified that error appears in the above-identified patent and that said Letters Patent is hereby corrected as shown below:

Replace Figs. 12A-C with the following Figs. 12A-C:

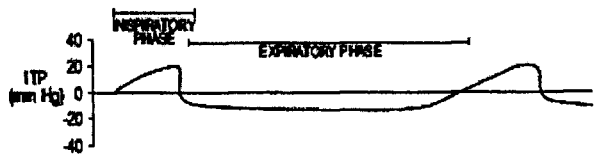

FIG. 12A

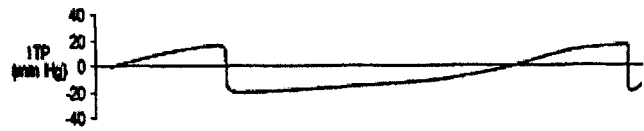

FIG. 12B

FIG. 12C

Signed and Sealed this
First Day of March, 2011

David J. Kappos
*Director of the United States Patent and Trademark Office*